US012765935B2

(12) United States Patent
Tan

(10) Patent No.: US 12,765,935 B2
(45) Date of Patent: Oct. 20, 2026

(54) TISSUE ABLATION APPARATUS, AND ELECTROCHEMICAL IMPEDANCE MEASUREMENT APPARATUS AND METHOD

(71) Applicant: SHENZHEN PULSECARE MEDICAL TECHNOLOGY CO., LTD., Shenzhen (CN)

(72) Inventor: Jianwen Tan, Shenzhen (CN)

(73) Assignee: SHENZHEN PULSECARE MEDICAL TECHNOLOGY CO., LTD., Shenzhen (CN)

(*) Notice: Subject to any disclaimer, the term of this patent is extended or adjusted under 35 U.S.C. 154(b) by 138 days.

(21) Appl. No.: 19/019,349

(22) Filed: Jan. 13, 2025

(65) Prior Publication Data

US 2025/0195127 A1 Jun. 19, 2025

Related U.S. Application Data

(63) Continuation of application No. PCT/CN2023/080596, filed on Mar. 9, 2023.

(30) Foreign Application Priority Data

Jul. 12, 2022 (CN) ......................... 202210816533.1

(51) Int. Cl.
*A61B 18/12* (2006.01)
*A61B 17/00* (2006.01)
(Continued)

(52) U.S. Cl.
CPC ............. *A61B 18/12* (2013.01); *G16H 20/40* (2018.01); *A61B 2017/00154* (2013.01);
(Continued)

(58) Field of Classification Search
CPC ................ A61B 18/12; A61B 18/1206; A61B 2017/00154; A61B 2018/00351;
(Continued)

(56) References Cited

U.S. PATENT DOCUMENTS

2015/0320481 A1 11/2015 Cosman, Jr. et al.
2019/0117964 A1* 4/2019 Bahrami ............... A61N 1/327
(Continued)

FOREIGN PATENT DOCUMENTS

CN 107872982 A 4/2018
CN 112236192 A 1/2021
(Continued)

OTHER PUBLICATIONS

The Extended European Search Report Issued on Jun. 5, 2026 for Corresponding European Patent Application No. 23838433.3.
(Continued)

*Primary Examiner* — Tigist S Demie

(57) ABSTRACT

Provided are a tissue ablation apparatus and an electrochemical impedance measurement apparatus and method. In the present application, a Faraday current participating in an electrochemical reaction of a target tissue and a voltage difference between a first output end and a second output end of a high-voltage pulse module are detected in real time, a corresponding electrochemical impedance parameter of the target tissue can be obtained according to an electrochemical impedance fitting function, and the amount of bubbles generated during ablation of the target tissue can be obtained according to the electrochemical impedance parameter of the target tissue, so that feedback control can be implemented for an outputted high-voltage pulse signal, to control the amount of generated bubbles in a timely manner.

20 Claims, 12 Drawing Sheets

(51) Int. Cl.
*G16H 20/40* (2018.01)
*A61B 18/00* (2006.01)

(52) U.S. Cl.
CPC ............... *A61B 2018/00577* (2013.01); *A61B 2018/00642* (2013.01); *A61B 2018/00678* (2013.01); *A61B 2018/00767* (2013.01); *A61B 2018/00827* (2013.01); *A61B 2018/00875* (2013.01)

(58) Field of Classification Search
CPC .......... A61B 2018/00577; A61B 2018/00613; A61B 2018/00642; A61B 2018/00678; A61B 2018/00702; A61B 2018/0072; A61B 2018/00767; A61B 2018/00827; A61B 2018/00839; A61B 2018/00875; A61B 2018/00892; A61B 5/0537; G16H 20/40
See application file for complete search history.

(56) References Cited

U.S. PATENT DOCUMENTS

| | | | | |
|---|---|---|---|---|
| 2019/0336757 | A1* | 11/2019 | Rodriguez | ........... A61N 1/0412 |
| 2022/0031387 | A1 | 2/2022 | Govari | |

FOREIGN PATENT DOCUMENTS

| | | | |
|---|---|---|---|
| CN | 114983551 | A | 9/2022 |
| CN | 115177357 | A | 10/2022 |
| CN | 115192182 | A | 10/2022 |
| CN | 217907965 | U | 11/2022 |
| CN | 217907966 | U | 11/2022 |

OTHER PUBLICATIONS

International Search Report and Written Opinion for Corresponding PCT Application No. PCT/CN2023/080596.

* cited by examiner

TISSUE ABLATION APPARATUS, AND ELECTROCHEMICAL IMPEDANCE MEASUREMENT APPARATUS AND METHOD

CROSS-REFERENCE TO RELATED APPLICATIONS

The present application is a Continuation Application of International Application No. PCT/CN2023/080596, filed on Mar. 9, 2023, claims priority to Chinese Patent Application No. 202210816533.1 entitled "Tissue Ablation Apparatus and Electrochemical Impedance Measurement Apparatus", filed with China National Intellectual Property Administration on Jul. 12, 2022, which is incorporated herein by reference in its entirety.

TECHNICAL FIELD

The present application relates to the technical field of tissue ablation, and particularly to a tissue ablation apparatus and electrochemical impedance measurement apparatus and method.

BACKGROUND

At present, vascular catheter ablation has been widely recognized as an effective method for treating arrhythmia. The purpose of ablation is to destroy tissues at risk of arrhythmia, to prevent abnormal electrical signals from propagating or destroy abnormal electrical signal conduction in cardiac tissue.

Pulsed electric field ablation has been proposed in recent years, which is a novel tissue ablation approach based on physical energy factors and mainly relies on irreversible electroporation. According to this approach, a high-voltage pulsed electric field is applied to cells to induce irreversible electroporation of cell membranes that leads to cell death, thus achieving tissue ablation. Due to different tissues have different electrical characteristics, pulsed electric field ablation has better tissue selectivity. For example, myocardial tissue is more sensitive to a high-voltage pulsed electric field, and neural tissue has higher tolerance to a pulsed electric field. Therefore, selective tissue ablation, such as ablation of tumor tissue close to nerves and blood vessels, can be realized by selecting a high-voltage pulsed electric field with an appropriate intensity.

However, in practice, during irreversible electroporation in pulsed electric field ablation, an amount of heat is generated or even a spark discharge occurs between the electrode and the tissue. Particularly, pulse parameters of irreversible electroporation (mainly including pulse voltage, pulse width, pulse interval time, etc.) directly affect the generation of heat and the temperature rise of the electrode and the tissue. In pulsed electric field ablation for treating patients with atrial fibrillation, heat generated by the electrode may lead to the generation of bubbles in blood, posing a serious risk of stroke to the patient. The generation of bubbles during discharge in the blood is not only caused by the heat generated by the electrode, but is also mainly due to an electrochemical reaction that occurs between the electrode and blood (as an electrolyte solution). When the electrochemical reaction occurs between the electrode and the blood interface, hydrogen or oxygen is generated.

In addition, the generation of bubbles during pulsed electric field ablation is also affected by other factors, and is not only related to the pulse energy and the pulse parameters, but also related to trace components in blood, the flow rate of blood etc. The key to controlling the generation of bubbles during pulsed electric field ablation is not to adjust the discharge energy or the pulse parameters, but is to monitor whether the pulse energy generated by bubbles reaches a threshold, or monitor trace bubbles online in real time. As long as the generation of trace bubbles can be detected, the pulse energy and the pulse parameters can be conveniently adjusted to control the further generation of bubbles, thereby ensure the life safety of the patient. However, at present, no method has been proposed for real-time monitoring of trace bubbles in blood during pulsed electric field ablation.

SUMMARY

Technical Problem

An objective of the present application is to provide a tissue ablation apparatus and an electrochemical impedance measurement apparatus and method, to solve the problem in the prior art that trace bubbles cannot be monitored in real time during pulsed electric field ablation.

Technical Solution

To achieve the above objective, the present application provides the following technical solutions. A first aspect of the embodiments of the present application provides a tissue ablation apparatus, including: a high-voltage pulse module, configured to generate a high-voltage pulse signal according to a pulse control signal, and apply the high-voltage pulse signal to a target tissue through a first output end and a second output end of the high-voltage pulse module, where the first output end is configured to connect to a first electrode, and the second output end is configured to connect to a second electrode; a Faraday current detection module, arranged between the high-voltage pulse module and the first electrode and the second electrode, and configured to generate a sampling signal based on a current flowing through the first electrode and a current flowing through the second electrode; a differential sampling module, connected to the first output end and the second output end of the high-voltage pulse module, and configured to generate and output a first feedback voltage and a second feedback voltage according to a voltage change of the first output end and a voltage change of the second output end respectively; a voltage processing module, connected to the differential sampling module and configured to generate and output a voltage feedback signal according to the first feedback voltage and the second feedback voltage, where the voltage feedback signal corresponds to a voltage difference between the first output end and the second output end; a high-frequency sampling module, connected to the voltage processing module and the Faraday current detection module, and configured to generate and output a digital feedback signal according to the voltage feedback signal and the sampling signal; and a main control module, connected to the high-voltage pulse module and the high-frequency sampling module, and configured to obtain a Faraday current and the voltage difference between the first output end and the second output end according to the received digital feedback signal, obtain an electrochemical impedance parameter of the target tissue by the Faraday current, the voltage difference between the first output end and the second output end and an electrochemical impedance fitting function, and generate the pulse control signal according to the electrochemical impedance parameter, where the electrochemical impedance fitting function is obtained by fitting electrical parameters obtained in a pulsed electric field ablation simulation experiment performed based on an equivalent circuit model of the target tissue.

A second aspect of the embodiments of the present application provides an electrochemical impedance measurement apparatus, applied to a tissue ablation apparatus to acquire an electrochemical impedance parameter of a target tissue, the electrochemical impedance measurement apparatus including: an output unit, configured to apply a high-voltage pulse signal to the target tissue through an electrode pair; a detection unit, configured to acquire a Faraday current and a voltage difference between the electrode pair from the side of the electrode pair; and an analysis unit, configured to obtain the electrochemical impedance parameter corresponding to the target tissue by the Faraday current, the voltage difference and an electrochemical impedance fitting function, where the electrochemical impedance fitting function is obtained by fitting electrical parameters obtained in a pulsed electric field ablation simulation experiment performed based on an equivalent circuit model of the target tissue.

A third aspect of the embodiments of the present application provides a electrochemical impedance measurement method, applied to a tissue ablation apparatus to acquire an electrochemical impedance parameter of a target tissue, the electrochemical impedance measurement method including: applying a high-voltage pulse signal to the target tissue through an electrode pair; acquiring a Faraday current and a voltage difference between the electrode pair from the side of the electrode pair; and obtaining the electrochemical impedance parameter corresponding to the target tissue by the Faraday current, the voltage difference and an electrochemical impedance fitting function, where the electrochemical impedance fitting function is obtained by fitting electrical parameters obtained in a pulsed electric field ablation simulation experiment performed based on an equivalent circuit model of the target tissue.

In an embodiment, obtaining of the electrochemical impedance fitting function by fitting electrical parameters obtained in the pulsed electric field ablation simulation experiment performed based on the equivalent circuit model of the target tissue includes steps of: establishing the equivalent circuit model of the target tissue; and performing a plurality of pulsed electric field ablation simulation experiments through the equivalent circuit model, and performing curve fitting according to the Faraday currents, the voltage differences, and the electrochemical impedance parameters of the equivalent circuit model obtained in the experiments to obtain the electrochemical impedance fitting function.

In an embodiment, the step of performing the plurality of pulsed electric field ablation simulation experiments through the equivalent circuit model, and performing curve fitting according to the Faraday currents, the voltage differences, and the electrochemical impedance parameters of the equivalent circuit model obtained in the experiments to obtain the electrochemical impedance fitting function includes: acquiring a plurality of sets of digital feedback signals in response to application of different high-voltage pulse signals or setting of different equivalent circuit models; obtaining a Faraday current and a voltage difference corresponding to each set of digital feedback signals, and performing curve fitting according to the Faraday currents and the voltage differences corresponding to the plurality of sets of digital feedback signals, and corresponding electrochemical impedance parameters of the equivalent circuit models to obtain the electrochemical impedance fitting function.

Beneficial Effects

The present application has the following beneficial effects.

A Faraday current participating in an electrochemical reaction of a target tissue and a voltage difference between a first output end and a second output end of a high-voltage pulse module are detected in real time, a corresponding electrochemical impedance parameter of the target tissue can be obtained according to an electrochemical impedance fitting function, and the amount of bubbles generated during ablation of the target tissue can be obtained according to the electrochemical impedance parameter of the target tissue, so that feedback control can be implemented for an outputted high-voltage pulse signal, to control the amount of generated bubbles in a timely manner. According to the present application, the status of bubble generation can be obtained while a high-voltage pulse signal is outputted for tissue ablation, there is no need to generate an additional detection signal, and high working efficiency is achieved. According to the present application, when data in the electrochemical impedance parameter exceeds a safety threshold, i.e., when the amount of bubbles generated exceeds a threshold, the output of the high-voltage pulse signal is stopped in a timely manner, to ensure the safety of the patient.

BRIEF DESCRIPTION OF DRAWINGS

To describe the technical solutions of the embodiments of the present application more clearly, the following briefly introduces the accompanying drawings required for describing the embodiments of the present application. Apparently, the accompanying drawings in the following description show only some embodiments of the present application, and a person of ordinary skill in the art may still derive other drawings from these accompanying drawings without creative efforts.

LIST OF REFERENCE NUMERALS

Figure 1:
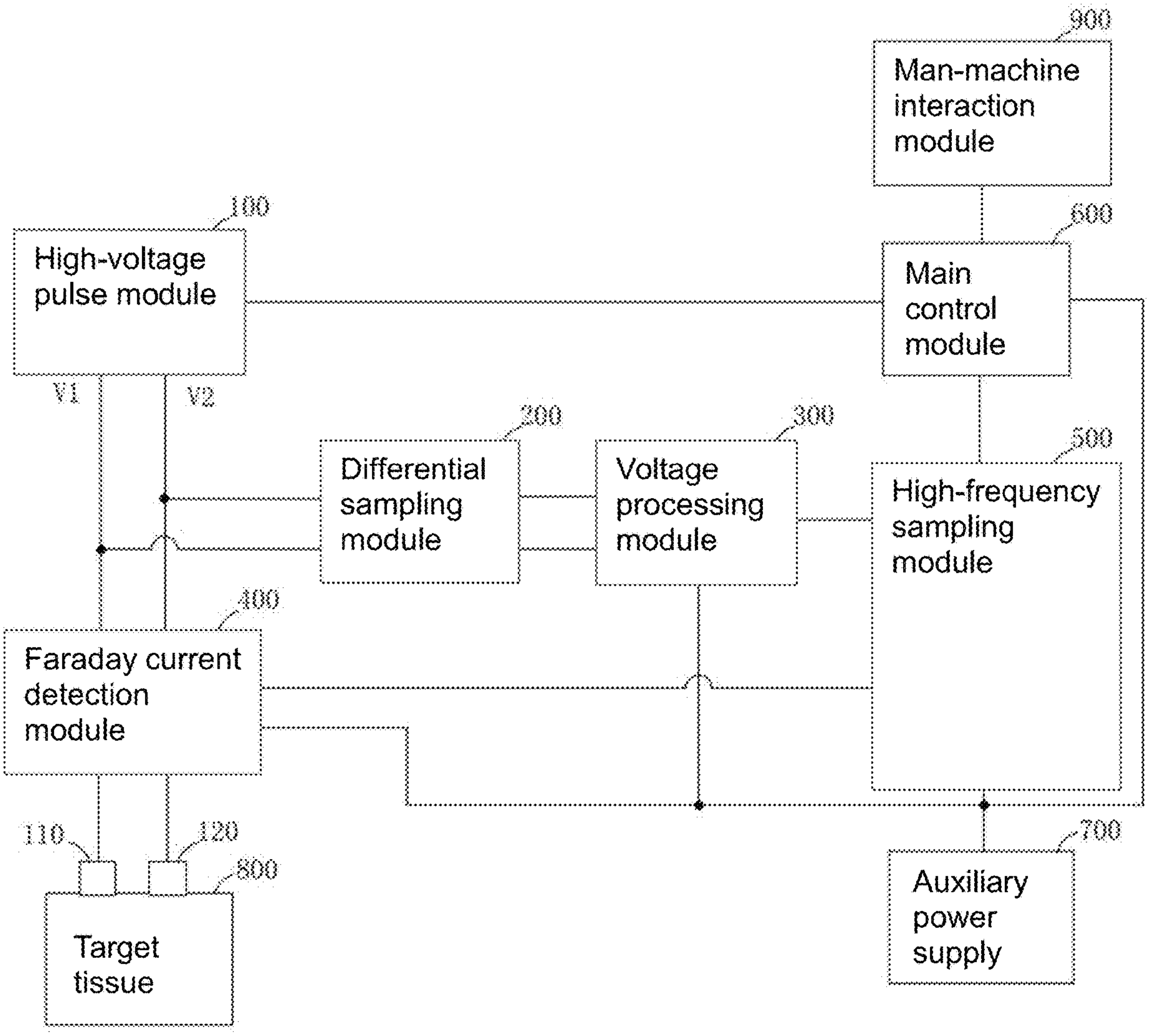
FIG. 1 is a principle schematic view of a tissue ablation apparatus according to a first embodiment of the present application.

100—high-voltage pulse module; 110—first electrode; 120—second electrode; 200—differential sampling module; 210—first sampling branch; 211—first broadband voltage divider unit; 212—first single-ended amplification unit; 220—second sampling branch; 221—second broadband voltage divider unit; 222—second single—ended amplification unit; 230—first protection unit; 240—second protection unit; 300—voltage processing module; 310—differential amplification unit; 320—third protection unit; 400—Faraday current detection module; 410—first differential voltage sampling unit; 420—second differential voltage sampling unit; 430—first current sampling probe; 440—second current sampling probe; 451—coupling coil; 452—load unit; 500—high-frequency sampling module; 510—filtering and shaping unit; 520—measuring range selection unit; 530—AD conversion unit; 540—sampling processing unit; 550—optical fiber transmission module; 600—main control module; 700—auxiliary power supply; 800—target tissue; 900—man-machine interaction module; 1000—electrochemical impedance measurement apparatus; 1100—output unit; 1200—detection unit; 1300—analysis unit; 1310—first analysis module; 1320—second analysis module; 1321—first calculation module; 1322—second calculation module.

DESCRIPTION OF EMBODIMENTS

To make the technical problems to be solved by the present application, technical solutions, and beneficial effects more comprehensible, the following further describes the present application in detail with reference to the accompanying drawings and embodiments. It should be understood that the specific embodiments described herein are merely used for explaining the present application, and are not intended to limit the present application.

It should be noted that, when an element is expressed as being "fixed to" or "arranged on" another element, the element may be directly on the another element, or one or more intermediate elements may be present between the element and the another element. When an element is expressed as being "connected to" another element, the element may be directly or indirectly connected to the another element.

It should be understood that orientation or position relationships indicated by the terms such as "length", "width", "on", "below", "front", "rear", "left", "right", "vertical", "horizontal", "top", "bottom", "inner", and "outer" are based on orientation or position relationships shown in the accompanying drawings, and are used only for ease and brevity of illustration and description, rather than indicating or implying that the mentioned apparatus or component need to have a particular orientation or need to be constructed and operated in a particular orientation. Therefore, such terms should not be construed as limiting of the present application.

Furthermore, the terms "first", and "second" are used merely for the purpose of description, and shall not be construed as indicating or implying relative importance or implying a quantity of indicated technical features. Therefore, a feature limited by "first" or "second" may explicitly or implicitly include one or more of the features. In the description of the present application, "a plurality of" means two or more, unless explicitly specified.

FIG. 1 is a schematic view illustrating the principle of a tissue ablation apparatus according to a first embodiment of the present application. For ease of description, only the part related to this embodiment is shown. A detail description is given below.

A tissue ablation apparatus includes a high-voltage pulse module 100, a differential sampling module 200, a voltage processing module 300, a Faraday current detection module 400, a high-frequency sampling module 500, and a main control module 600.

The high-voltage pulse module 100 is configured to generate a high-voltage pulse signal according to a pulse control signal, and apply the high-voltage pulse signal to a target tissue 800 through a first output end V1 and a second output end V2 of the high-voltage pulse module 100, where the first output end is configured to connect to a first electrode 110, and the second output end is configured to connect to a second electrode 120. The target tissue 800 may be a biological tissue. An amplitude range of the high-voltage pulse signal is 0.5 V to 5 kV, and a pulse width of the high-voltage pulse signal is 0.5 μs to 200 μs. The first electrode 110 and the second electrode 120 may be electrode needles. The Faraday current detection module 400 is arranged between the high-voltage pulse module 100 and the first electrode 110 and the second electrode 120, and is configured to generate a sampling signal based on a difference between a current flowing through the first electrode 110 and a current flowing through the second electrode 120. The difference between the currents corresponds to a Faraday current IF participating in an electrochemical reaction of the target tissue 800. The differential sampling module 200 is connected to the first output end V1 and the second output end V2 of the high-voltage pulse module 100, and is configured to generate and output a first feedback voltage and a second feedback voltage respectively according to a voltage change of the first output end V1 and a voltage change of the second output end V2. The voltage processing module 300 is connected to the differential sampling module 200 and is configured to generate and output a voltage feedback signal according to the first feedback voltage and the second feedback voltage, where the voltage feedback signal corresponds to a voltage difference between the first output end V1 and the second output end V2. The high-frequency sampling module 500 is connected to the voltage processing module 300 and the Faraday current detection module 400, and is configured to generate and output a digital feedback signal according to the voltage feedback signal and the sampling signal. The main control module 600 is connected to the high-voltage pulse module 100 and the high-frequency sampling module 500, and is configured to obtain the Faraday current IF and the voltage difference between the first output end V1 and the second output end V2 according to the received digital feedback signal, obtain an electrochemical impedance parameter of the target tissue 800 by the Faraday current IF, the voltage difference between the first output end V1 and the second output end V2 and an electrochemical impedance fitting function, and generate the pulse control signal according to the electrochemical impedance parameter. The main control module 600 may be an industrial computer, a single-chip microcomputer, or a microcontroller. The electrochemical impedance fitting function may be obtained by fitting electrical parameters obtained in a pulsed electric field ablation simulation experiment performed based on an equivalent circuit model of the target tissue 800.

It should be noted that, when the high-voltage pulse signal is applied to the target tissue 800, the electrodes discharge in the blood, and at the same time, an oxidation-reduction reaction occurs on the surface of the electrodes, which leads to the generation of bubbles and changes the electrochemical impedance parameter of the target tissue 800. According to the electrochemical theory, the number of electrons passing through the electrodes and the blood in the oxidation-reduction reaction process is related to the degree of chemical reaction, and the consumption of the reactants in the reaction is related to the amount of gas or other products generated. If an electrochemical reaction such as an oxidation-reduction reaction occurs in the target tissue 800, there will be a difference between the current flowing through the first electrode 110 and the current flowing through the second electrode 120. The difference between the currents is the Faraday current IF participating in the electrochemical reaction of the target tissue 800. Therefore, the electrochemical impedance parameter obtained by using the electrochemical impedance fitting function according to the Faraday current IF and the voltage difference between the first output end V1 and the second output end V2 can well reflect the amount of bubbles generated. Therefore, when part of data in the electrochemical impedance parameter exceeds a preset threshold, the main control module 600 may generate a corresponding pulse control signal in real time, to adjust the high-voltage pulse signal or stop outputting the high-voltage pulse signal.

In this embodiment, as shown in FIG. 1, the tissue ablation apparatus further includes an auxiliary power supply 700. The auxiliary power supply 700 is connected to the voltage processing module 300, the Faraday current detection module 400, the high-frequency sampling module 500, and the main control module 600. The auxiliary power supply 700 is configured to generate a plurality of levels of operating voltage, to supply power to the voltage processing module 300, the Faraday current detection module 400, the high-frequency sampling module 500, and the main control module 600.

In this embodiment, as shown in FIG. 1, the tissue ablation apparatus further includes a man-machine interaction module 900. The man-machine interaction module 900 is connected to the main control module 600. The man-machine interaction module 900 may be a device such as a touch screen and a physical key, and is configured to input a related parameter to the main control module 600 and display tissue ablation parameters of the main control module 600 and the obtained electrochemical impedance parameter of the target tissue 800.

Figure 2:
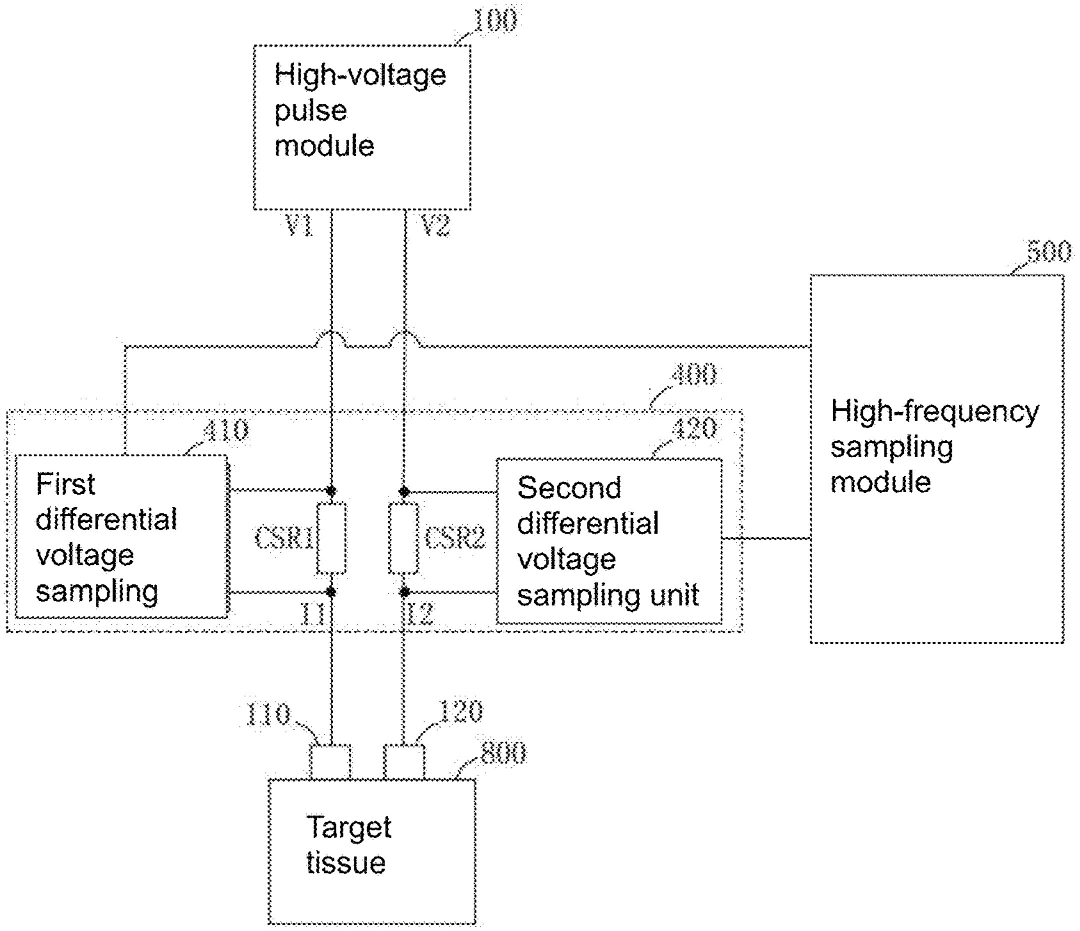
FIG. 2 is a principle schematic view of a Faraday current detection module according to the first embodiment of the present application.

In this embodiment, as shown in FIG. 2, the Faraday current detection module 400 includes a first sampling resistor CSR1, a second sampling resistor CSR2, a first differential voltage sampling unit 410, and a second differential voltage sampling unit 420. The first sampling resistor CSR1 is connected in series between the first output end V1 and the first electrode 110. The second sampling resistor CSR2 is connected in series between the second output end V2 and the second electrode 120. The first differential voltage sampling unit 410 is connected to the high-frequency sampling module 500 and two ends of the first sampling resistor CSR1. The second differential voltage sampling unit 420 is connected to the high-frequency sampling module 500 and two ends of the second sampling resistor CSR2. The first differential voltage sampling unit 410 is configured to collect a first voltage difference between the two ends of the first sampling resistor CSR1. The second differential voltage sampling unit 420 is configured to collect a second voltage difference between the two ends of the second sampling resistor CSR2. In an example, the first differential voltage sampling unit 410 and the second differential voltage sampling unit 420 are each a differential amplification circuit using an operational amplifier. The high-frequency sampling module 500 is configured to generate and output the digital feedback signal based on the first voltage difference and the second voltage difference. The main control module 600 is configured to obtain the Faraday current IF participating in an electrochemical reaction of the target tissue 800 based on the digital feedback signal, a resistance value of the first sampling resistor CSR1, and a resistance value of the second sampling resistor CSR2.

Figure 3:
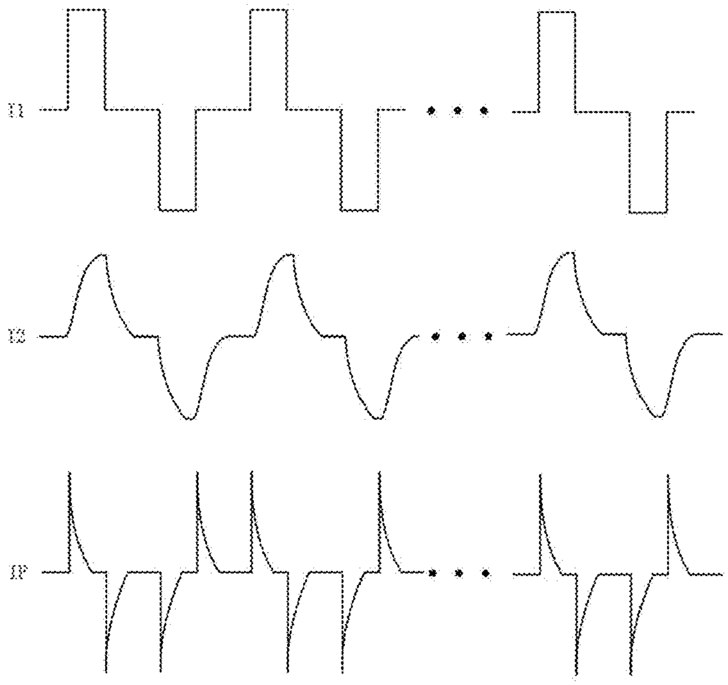
FIG. 3 is a schematic view of a current waveform according to the first embodiment of the present application.

Particularly, the main control module 600 may obtain the first voltage difference and the second voltage difference from the digital feedback signal. When the resistance values of the first sampling resistor CSR1 and the second sampling resistor CSR2 are known parameters, a first current I1 flowing through the first sampling resistor CSR1 and a second current I2 flowing through the second sampling resistor CSR2 may be calculated. The first current I1 is equal to the current flowing through the first electrode 110. The second current I2 is equal to the current flowing through the second electrode 120. For example, when the first current I1 is an output current and the second current I2 is an input current, waveforms of the first current I1, the second current I2, and the Faraday current IF are as shown in FIG. 3. The corresponding Faraday current IF can be obtained by subtracting the second current I2 from the first current I1.

Figure 4:
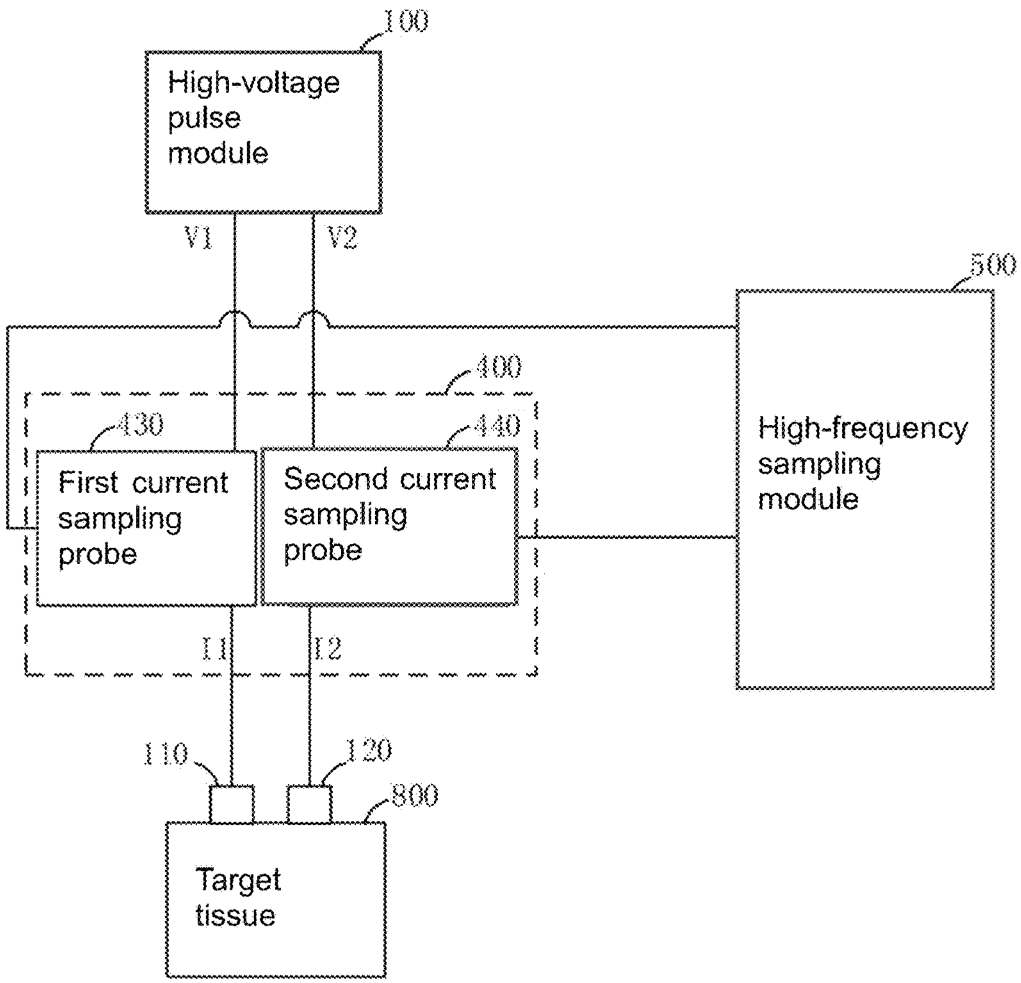
FIG. 4 is a principle schematic view of a Faraday current detection module according to another embodiment of the present application.

In another embodiment, as shown in FIG. 4, the Faraday current detection module 400 includes a first current sampling probe 430 and a second current sampling probe 440. The first current sampling probe 430 is arranged on a wire between the first output end V1 and the first electrode 110 and is electrically connected to the high-frequency sampling module 500. The second current sampling probe 440 is arranged on a wire between the second output end V2 and the second electrode 120 and is electrically connected to the high-frequency sampling module 500.

The first current sampling probe 430 is configured to generate a first current feedback signal based on a current flowing through the wire between the first output end V1 and the first electrode 110 and output the first current feedback signal to the high-frequency sampling module 500. The second current sampling probe 440 is configured to generate a second current feedback signal based on a current flowing through the wire between the second output end V2 and the second electrode 120 and output the second current feedback signal to the high-frequency sampling module 500. The sampling signal includes the first current feedback signal and the second current feedback signal. The high-frequency sampling module 500 is configured to generate and output the digital feedback signal based on the first current feedback signal and the second current feedback signal. The main control module 600 is configured to obtain the currents on the two wires based on the digital feedback signal, and obtain the Faraday current participating in the electrochemical reaction of the target tissue according to the currents on the two wires.

Through the coupling of the first current sampling probe 430 and the second current sampling probe 440 with the wires to detect the currents, the impact on related sampled electrical parameters and circuits can be reduced, so as not to affect the normal operation of the tissue ablation apparatus.

Figure 5:
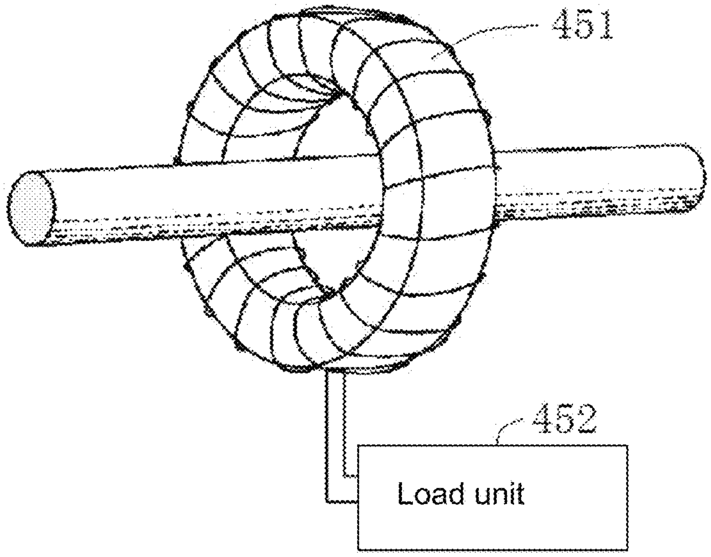
FIG. 5 is a schematic structural view of a coupling coil according to an embodiment of the present application.

In an example, as shown in FIG. 5, the first current sampling probe 430 and the second current sampling probe 440 have the same structure, both including a coupling coil 451 and a load unit 452. The coupling coil 451 may be sleeved on the wire connected to the first output end V1 or the second output end V2. An output end of the coupling coil 451 is connected to the load unit 452. The load unit 452 is further connected to the high-frequency sampling module 500. The coupling coil 451 is configured to generate an induction current according to the current flowing through the wire and output the induction current. The load unit 452 is configured to generate a current feedback signal according to the induction current and output the current feedback signal, i.e., the load unit 452 of the first current sampling probe 430 outputs the first current feedback signal, and the load unit 452 of the second current sampling probe 440 outputs the second current feedback signal.

Figure 6:
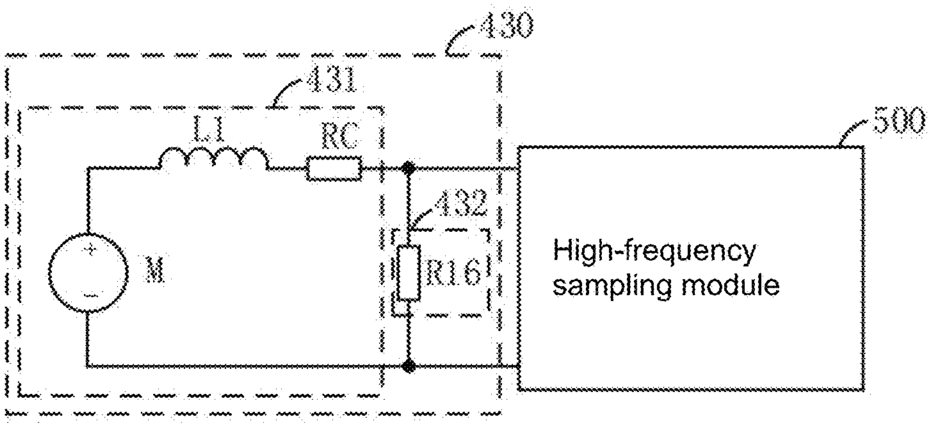
FIG. 6 is a schematic view of an equivalent circuit of a current sampling probe according to another embodiment of the present application.

Particularly, an equivalent circuit of the coupling coil 451 and the load unit 452 is as shown in FIG. 6. The coupling coil 451 may be a self-integrating Rogowski coil. The coupling coil 451 in the equivalent circuit includes an equivalent power supply M, an equivalent inductor L1, and an equivalent resistor RC connected in series in sequence. The load unit 452 may be a load resistor R16. The coupling coil 451 may be sleeved on the corresponding wire. Two induction current output ends of the coupling coil 451 (including one end of the equivalent power supply M and one end of the equivalent resistor RC) are respectively connected to two ends of the load unit 452 to output the induction current to the load unit 452. The two ends of the load unit 452 are connected to the high-frequency sampling module 500. When the induction current flows through the load unit 452, the high-frequency sampling module 500 may sample voltages (current feedback signals) at the two ends of the load unit 452 to obtain the corresponding current feedback signals, generate the corresponding digital feedback signal according to the current feedback signals, and output the corresponding digital feedback signal.

Figure 7:
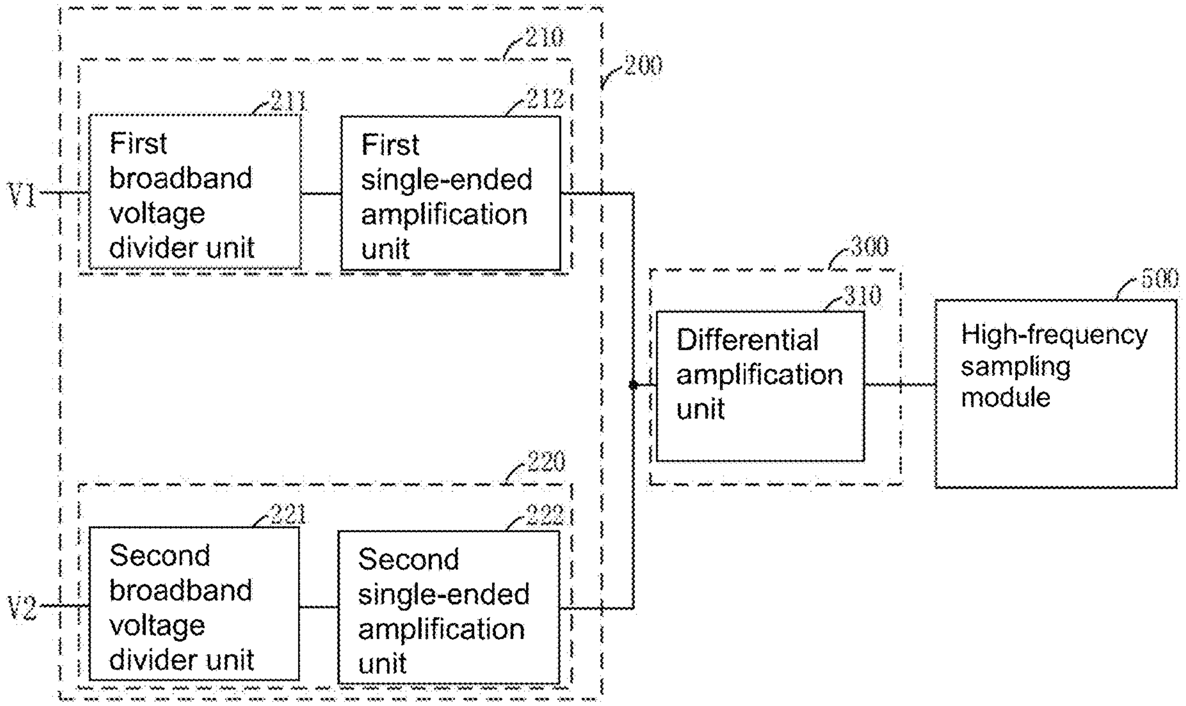
FIG. 7 is a principle schematic view of a differential sampling module and a voltage processing module according to the first embodiment of the present application.

In this embodiment, as shown in FIG. 7, the differential sampling module 200 includes a first sampling branch 210 and a second sampling branch 220. The first sampling branch 210 is connected between the first output end V1 and the voltage processing module 300. The second sampling branch 220 is connected between the second output end V2 and the voltage processing module 300. The first sampling branch 210 is configured to generate the first feedback voltage. The second sampling branch 220 is configured to generate the second feedback voltage.

The differential sampling module 200 may perform differential sampling on a bipolar high-voltage pulse signal, and at the same time, use the two independent sampling branches to respectively sample voltages at the first output end V1 and the second output end V2. As such, the voltage sampling at the first output end V1 does not interfere with the voltage sampling at the second output end V2, and an accurate first feedback voltage and an accurate second feedback voltage can be obtained.

In this embodiment, the first sampling branch 210 includes a first broadband voltage divider unit 211 and a first single-ended amplification unit 212. The first broadband voltage divider unit 211 respectively connected to the first output end V1 and the first single-ended amplification unit 212. The first single-ended amplification unit 212 is further connected to the voltage processing module 300. The first single-ended amplification unit 212 is configured to generate the first feedback voltage according to a voltage obtained through voltage division by the first broadband voltage divider unit 211. The second sampling branch 220 includes a second broadband voltage divider unit 221 and a second single-ended amplification unit 222. The second broadband voltage divider unit 221 is connected to the first output end V1 and the second single-ended amplification unit 222. The second single-ended amplification unit 222 is further connected to the voltage processing module 300. The second single-ended amplification unit 222 is configured to generate the second feedback voltage according to a voltage obtained through voltage division by the second broadband voltage divider unit 221.

It should be noted that because the voltage amplitude of the high-voltage pulse signal is too high, voltage dividing needs to be performed on the high-voltage pulse signal through the first broadband voltage divider unit 211 and the second broadband voltage divider unit 221. In addition, to acquire voltage signals of the first output end V1 and the second output end V2 without distortion, the first broadband voltage divider unit 211 and the second broadband voltage divider unit 221 have a high bandwidth, so that both high-frequency and low-frequency signals can be transmitted to the first single-ended amplification unit 212 or the second single-ended amplification unit 222 through the first broadband voltage divider unit 211 or the second broadband voltage divider unit 221. The first single-ended amplification unit 212 and the second single-ended amplification unit 222 may respectively amplify the voltages of the first output end V1 and the voltage of the second output end V2 obtained through voltage dividing by a certain multiple to obtain the first feedback voltage and the second feedback voltage. Amplification factors of the first single-ended amplification unit 212 and the second single-ended amplification unit 222 may be set according to the actual situation, and are not limited in this embodiment. In this embodiment, the first single-ended amplification unit 212 and the second single-ended amplification unit 222 may reach a gain-bandwidth product (GBWP) of 70 MHz, with a slew rate of 200 V/μs and a low-noise voltage of 6.3 nm/V Hz.

The first broadband voltage divider unit 211 includes a first low-frequency impedance voltage divider unit and a first high-frequency impedance voltage divider unit. The first low-frequency impedance voltage divider unit is connected to the first output end V1 and the first single-ended amplification unit 212. The first high-frequency impedance voltage divider unit is connected in parallel to the first low-frequency impedance voltage divider unit. The second broadband voltage divider unit 221 includes a second low-frequency impedance voltage divider unit and a second high-frequency impedance voltage divider unit. The second low-frequency impedance voltage divider unit is connected to the first output end V1 and the second single-ended amplification unit 222. The second high-frequency impedance voltage divider unit is connected in parallel to the second low-frequency impedance voltage divider unit. The first low-frequency impedance voltage divider unit is configured to perform voltage dividing on a low-frequency signal of the first output end V1. The second low-frequency impedance voltage divider unit is configured to perform voltage dividing on a low-frequency signal of the second output end V2. The first high-frequency impedance voltage divider unit is configured to perform voltage dividing on a high-frequency signal of the first output end V1. The second high-frequency impedance voltage divider unit is configured to perform voltage dividing on a high-frequency signal of the second output end V2. In this embodiment, even if the voltage amplitude of the high-voltage pulse signal is 5 kV, a maximum voltage obtained through voltage dividing by the first broadband voltage divider unit 211 and the second broadband voltage divider unit 221 still does not exceed 5 V, and voltage change statuses of the first output end V1 and the second output end V2 can also be maintained.

Figure 8:
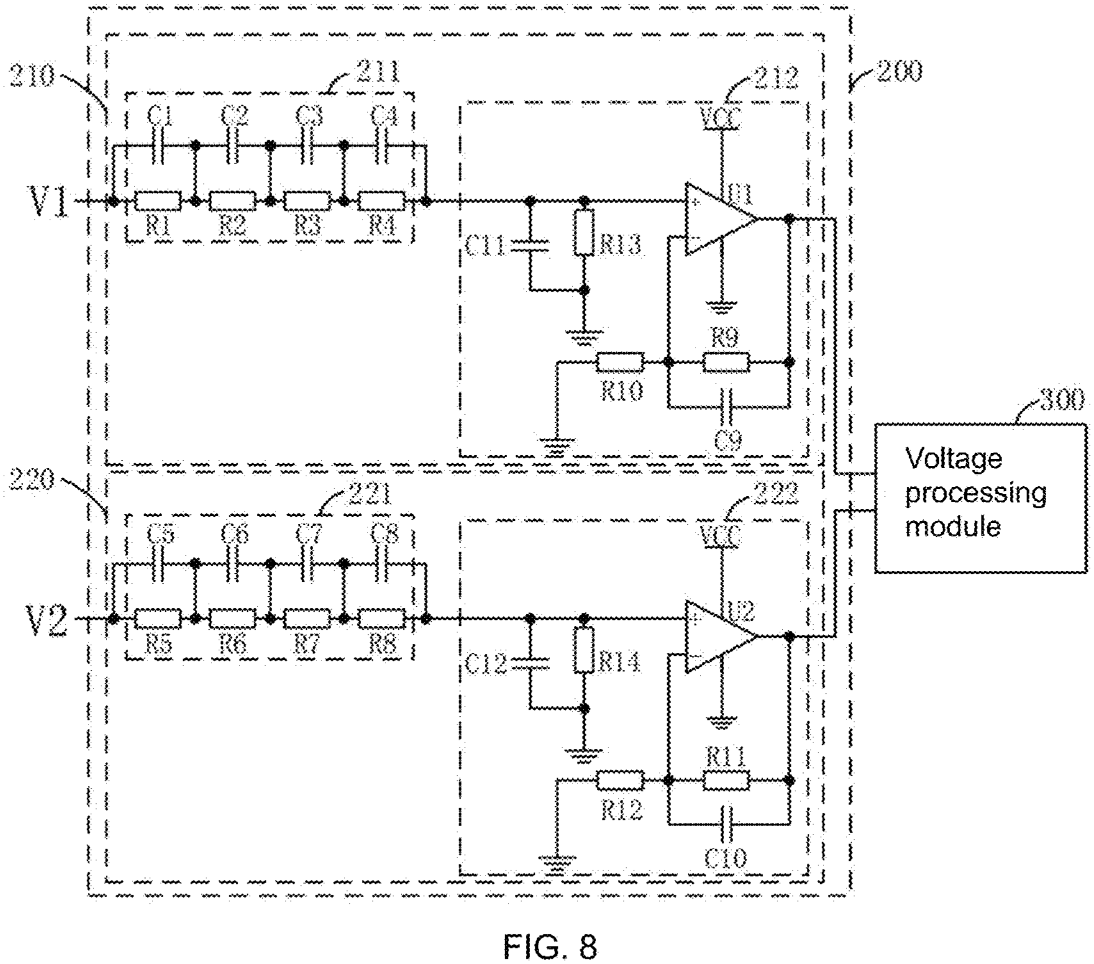
FIG. 8 is a schematic circuit view of the differential sampling module according to the first embodiment of the present application.

In an example, as shown in FIG. 8, the first low-frequency impedance voltage divider unit includes a resistor R1, a resistor R2, a resistor R3, and a resistor R4 connected in series in sequence. The resistor R1 is connected to the first output end V1. The resistor R4 is connected to the first single-ended amplification unit 212. The first high-frequency impedance voltage divider unit includes a capacitor C1, a capacitor C2, a capacitor C3, and a capacitor C4 connected in series in sequence. The capacitor C1, the capacitor C2, the capacitor C3, and the capacitor C4 are respectively in one-to-one correspondence with and connected in parallel to the resistor R1, the resistor R2, the resistor R3, and the resistor R4. The resistor R1, the resistor R2, the resistor R3, and the resistor R4 are all high-frequency non-inductive resistors. The capacitor C1, the capacitor C2, the capacitor C3, and the capacitor C4 are all capacitors with low equivalent inductance.

Particularly, both the first single-ended amplification unit 212 and the second single-ended amplification unit 222 are in-phase amplifier circuits. In an example, as shown in FIG. 8, the first single-ended amplification unit 212 includes a first operational amplifier U1, a first feedback resistor R9, and a second feedback resistor R10. A non-inverting input end of the first operational amplifier U1 is connected to the first broadband voltage divider unit 211. An output end of the first operational amplifier U1 is connected to the voltage processing module 300. A first end of the first feedback resistor R9 is connected to the output end of the first operational amplifier U1. A second end of the first feedback resistor R9 is connected to an inverting input end of the first operational amplifier U1. A first end of the second feedback resistor R10 is connected to the inverting input end of the first operational amplifier U1. A second end of the second feedback resistor R10 is connected to ground. The second single-ended amplification unit 222 includes a second operational amplifier U2, a third feedback resistor R11, and a fourth feedback resistor R12. A non-inverting input end of the second operational amplifier U2 is connected to the second broadband voltage divider unit 221. An output end of the second operational amplifier U2 is connected to the voltage processing module 300. A first end of the third feedback resistor R11 is connected to the output end of the second operational amplifier U2. A second end of the third feedback resistor R11 is connected to an inverting input end of the second operational amplifier U2. A first end of the fourth feedback resistor R12 is connected to the inverting input end of the second operational amplifier U2. A second end of the fourth feedback resistor R12 is connected to ground.

Figure 9:
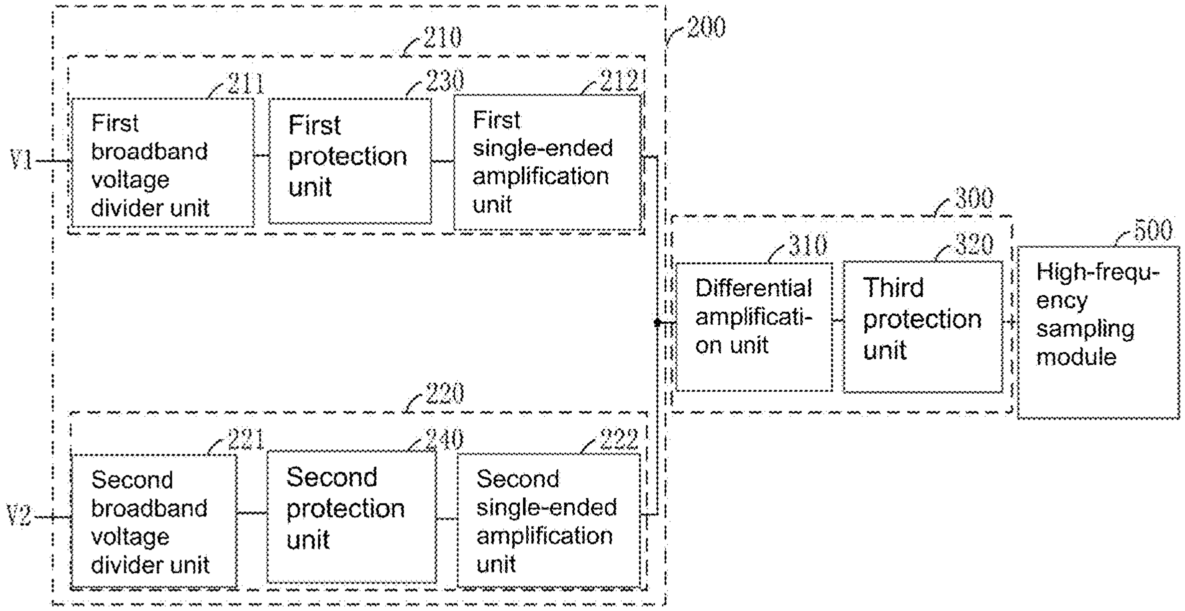
FIG. 9 is a principle schematic view of a protection unit according to another embodiment of the present application.

In another embodiment, as shown in FIG. 9, the first sampling branch 210 further includes a first protection unit 230, the second sampling branch 220 further includes a second protection unit 240, the first protection unit 230 is connected between the first broadband voltage divider unit 211 and the first single-ended amplification unit 212, and the second protection unit 240 is connected between the second broadband voltage divider unit 221 and the second single-ended amplification unit 222. The first protection unit 230 is configured to limit an amplitude of a voltage to be transmitted to the first single-ended amplification unit 212, and the second protection unit 240 is configured to limit an amplitude of a voltage to be transmitted to the second single-ended amplification unit 222. In this embodiment, the first protection unit 230 and the second protection unit 240 have the same circuit structure.

Figure 10:
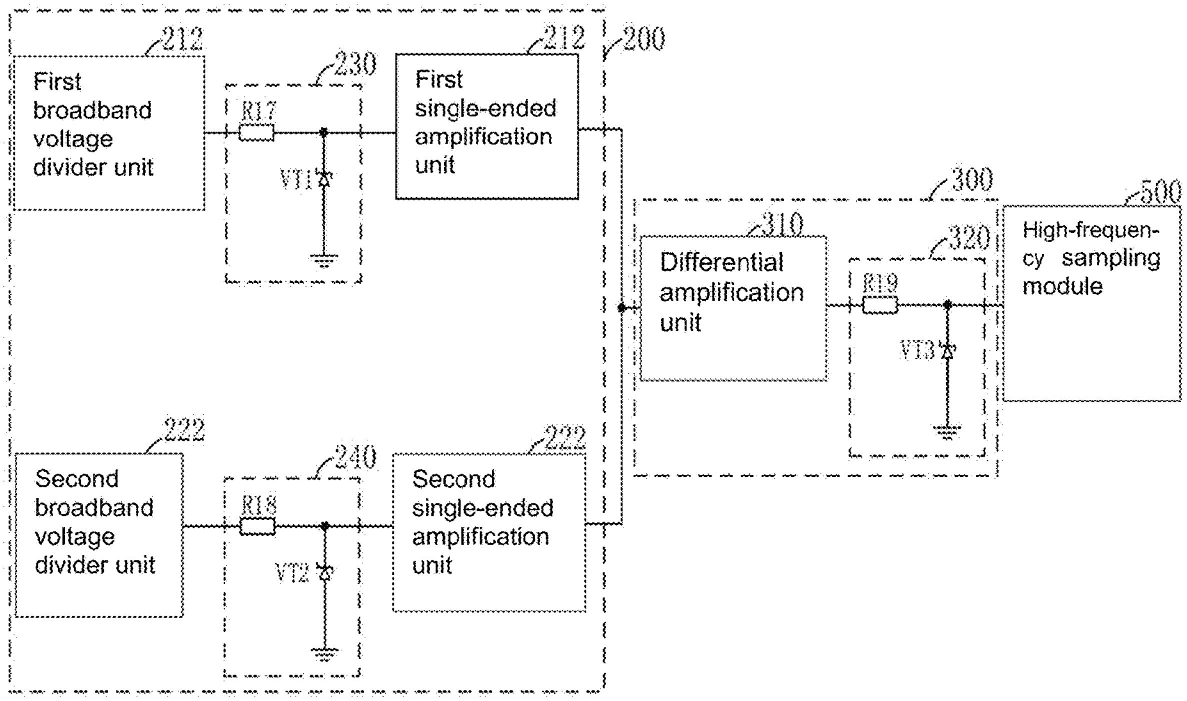
FIG. 10 is a schematic circuit view of a protection unit according to another embodiment of the present application.

In an example, as shown in FIG. 10, the first protection unit 230 includes a voltage divider resistor R17 and a breakdown diode VT1. A first end of the voltage divider resistor R17 is connected to the first broadband voltage divider unit 211. A second end of the voltage divider resistor R17 is connected to the first single-ended amplification unit 212. A negative electrode of the breakdown diode VT1 is connected to the second end of the voltage divider resistor R17. A positive electrode of the breakdown diode VT1 is connected to ground. When the amplitude of the voltage outputted by the first broadband voltage divider unit 211 is too high and is greater than a breakdown voltage of the breakdown diode VT1, the breakdown diode VT1 is broken down, so that the second end of the voltage divider resistor R17 is grounded to release the voltage. The second protection unit 240 includes a voltage divider resistor R18 and a breakdown diode VT2. A first end of the voltage divider resistor R18 is connected to the second broadband voltage divider unit 221. A second end of the voltage divider resistor R18 is connected to the second single-ended amplification unit 222. A negative electrode of the breakdown diode VT2 is connected to the second end of the voltage divider resistor R18. A positive electrode of the breakdown diode VT2 is connected to ground. When the amplitude of the voltage outputted by the second broadband voltage divider unit 221 is too high and is greater than a breakdown voltage of the breakdown diode VT2, the breakdown diode VT2 is broken down, so that the second end of the voltage divider resistor R18 is grounded to release the voltage.

In this embodiment, the voltage processing module 300 includes a differential amplification unit 310. The differential amplification unit 310 is connected to the differential sampling module 200 and the high-frequency sampling module 500. The differential amplification unit 310 is configured to generate the voltage feedback signal according to the first feedback voltage and the second feedback voltage.

It should be noted that, the differential amplification unit 310 may be a differential amplification circuit, and may amplify a voltage difference between the first feedback voltage and the second feedback voltage by a certain multiple, so as to generate the corresponding voltage feedback signal.

Figure 11:
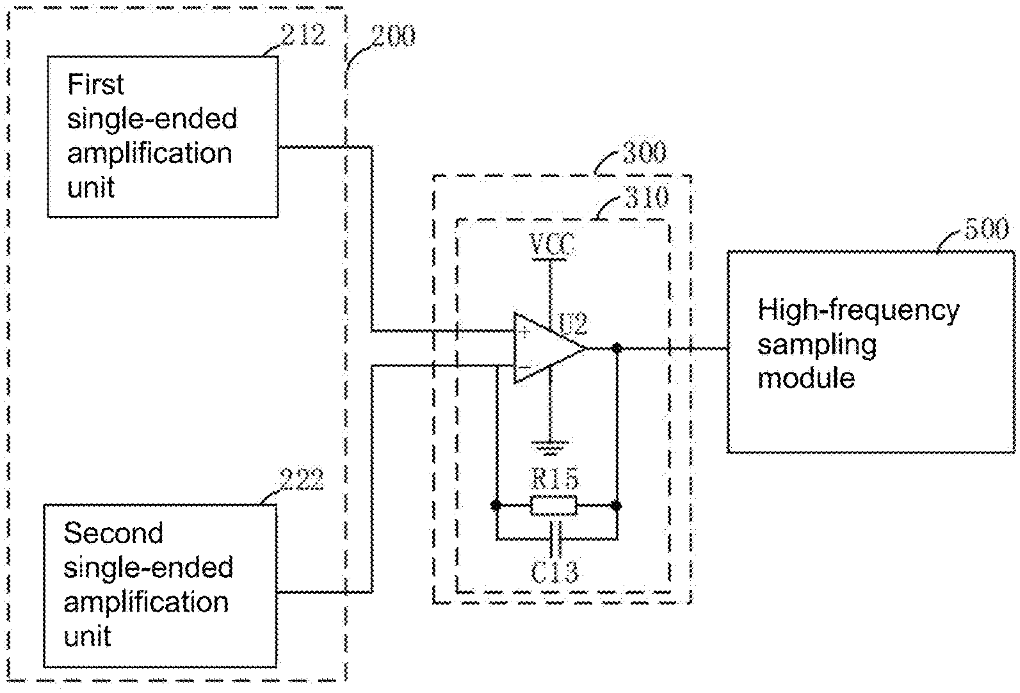
FIG. 11 is a schematic circuit view of a differential amplification unit according to the first embodiment of the present application.

In an example, as shown in FIG. 11, the differential amplification unit 310 includes a third operational amplifier U3 and a fifth feedback resistor R15. A non-inverting input end of the third operational amplifier U3 is connected to the first single-ended amplification unit 212. An inverting input end of the third operational amplifier U3 is connected to the second single-ended amplification unit 222. A first end of the fifth feedback resistor R15 is connected to an output end of the third operational amplifier U3. A second end of the fifth feedback resistor R15 is connected to the inverting input end of the third operational amplifier U3.

In another embodiment, as shown in FIG. 9 and FIG. 10, the voltage processing module 300 further includes a third protection unit 320. The third protection unit 320 is connected between the differential amplification unit 310 and the high-frequency sampling module 500. The third protection unit 320 is configured to limit an amplitude of a voltage to be transmitted to the high-frequency sampling module 500. The third protection unit 320 is configured to limit the amplitude of the voltage feedback signal. The first protection unit 230, the second protection unit 240, and the third protection unit 320 have the same structure.

Figure 12:
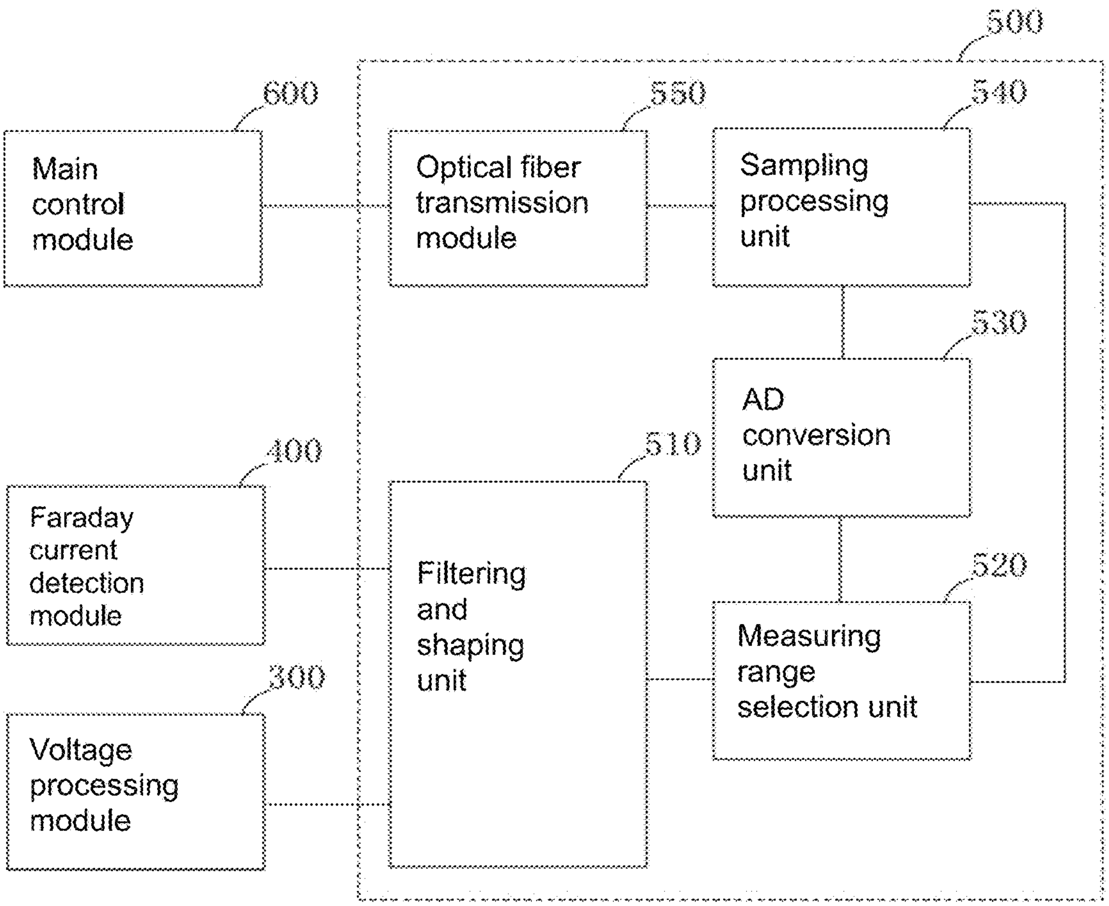
FIG. 12 is a principle schematic view of a high-frequency sampling module according to the first embodiment of the present application.

In this embodiment, as shown in FIG. 12, the high-frequency sampling module 500 includes a filtering and shaping unit 510, a measuring range selection unit 520, an analog-to-digital (AD) conversion unit 530, and a sampling processing unit 540 connected in sequence. The filtering and shaping unit 510 is connected to the voltage processing module 300 and the Faraday current detection module 400. The sampling processing unit 540 is connected to the main control module 600 and the measuring range selection unit 520. The sampling processing unit 540 is configured to generate a digital feedback signal according to the digital signal outputted by the AD conversion unit 530, and configure a measuring range of the measuring range selection unit 520 according to the digital feedback signal.

The filtering and shaping unit 510 is configured to filter and shape the voltage feedback signal and the sampling signal to reduce distortion of the voltage feedback signal and the sampling signal. The measuring range selection unit 520 is configured to convert the voltage feedback signal and the sampling signal according to a set measuring range and outputs an analog signal corresponding to an input measuring range of the AD conversion unit 530. The AD conversion unit 530 is configured to sample the analog signal according to a preset frequency, so as to convert the analog signal to the digital signal. The sampling processing unit 540 is configured to generate the digital feedback signal according to the digital signal, and configure the measuring range set by the measuring range selection unit 520 according to the digital feedback signal, to further improve the accuracy. The sampling processing unit 540 may be a field programmable gate array (FPGA) or a digital signal processing (DSP) unit.

The digital feedback signal includes a digital voltage signal and a digital sampling signal. The digital voltage signal corresponds to a voltage value between the first output end V1 and the second output end V2 (i.e., between two ends of the target tissue 800). The digital sampling signal corresponds to the first current I1 and the second current I2.

In this embodiment, the high-frequency sampling module 500 is further wrapped with a shielding shell configured to shield external electromagnetic signals.

In this embodiment, as shown in FIG. 12, the high-frequency sampling module 500 further includes an optical fiber transmission module 550 connected to the sampling processing unit 540. The optical fiber transmission module 550 is configured to communicably connect to the main control module 600, i.e., the sampling processing unit 540 is communicatively connected to the main control module 600 through the optical fiber transmission module 550.

Figure 13:
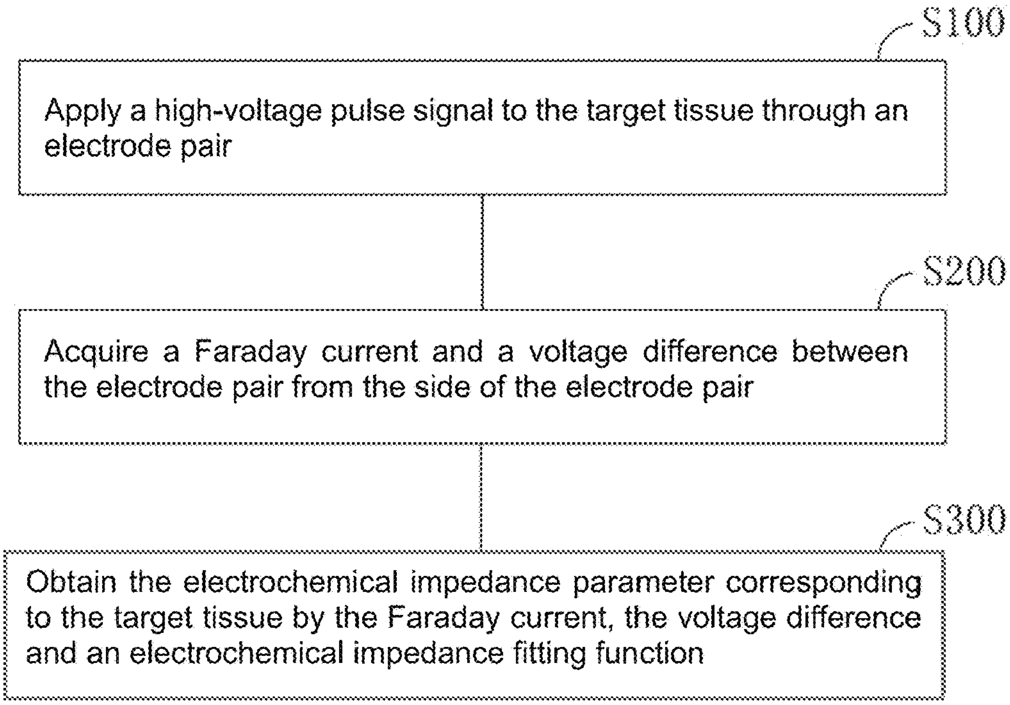
FIG. 13 is a flowchart of a electrochemical impedance measurement method according to a second embodiment of the present application.

FIG. 13 is a flowchart of a electrochemical impedance measurement method according to a second embodiment of the present application. For ease of description, only the part related to this embodiment is shown. A detail description is given below.

An electrochemical impedance measurement method is provided, which may be applied to the tissue ablation apparatus according to any one of the foregoing embodiments to acquire an electrochemical impedance parameter of a target tissue 800. The electrochemical impedance measurement method includes the following steps S100 to S300.

In S100, a high-voltage pulse signal is applied to the target tissue 800 through an electrode pair.

In S200, a Faraday current IF and a voltage difference between the electrode pair are acquired from the side of the electrode pair.

Figure 14:
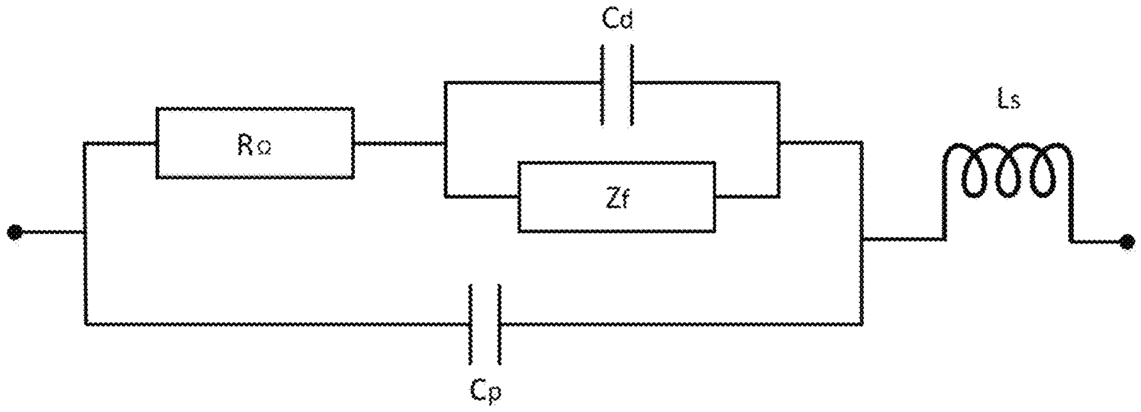
FIG. 14 is a schematic view of an equivalent circuit model according to the second embodiment of the present application.

In S300, the electrochemical impedance parameter corresponding to the target tissue 800 is obtained by the Faraday current IF, the voltage difference and an electrochemical impedance fitting function, The electrochemical impedance fitting function is obtained by fitting electrical parameters obtained in a pulsed electric field ablation simulation experiment performed based on an equivalent circuit model of the target tissue 800. The equivalent circuit model is as shown in FIG. 14. In this embodiment, electrochemical impedance parameters in the equivalent circuit model include a tissue and solution resistance RΩ, a Faraday impedance Zf, an electric double layer capacitance Cd, a parasitic capacitance Cp, and a parasitic inductance Ls. The Faraday impedance Zf represents a nonlinear impedance in the electrochemical reaction system, and parameters of the Faraday impedance Zf are related to the frequency of the high-voltage pulse signal. The electric double layer capacitance Cd represents an equivalent capacitance of ablation electrodes in the blood. The parasitic capacitance Cp and the parasitic inductance Ls respectively represent a parasitic capacitance and a parasitic inductance of the entire circuit.

It should be noted that, the electrochemical impedance model of the target tissue 800 is complex, includes a large number of parameters that cannot be directly detected. Therefore, to acquire the electrochemical impedance parameter of the target tissue 800 in real time, the method of acquiring the electrochemical impedance fitting function through curve fitting in this embodiment only requires the collection of the Faraday current IF and the voltage difference between the electrode pair that can be easily detected. The voltage difference between the electrode pair may be replaced with the voltage difference between the first output end V1 and the second output end V2. In this way, a real-time electrochemical impedance parameter can be obtained, and the status of bubble generation can be determined according to the real-time electrochemical impedance parameter.

Figure 15:
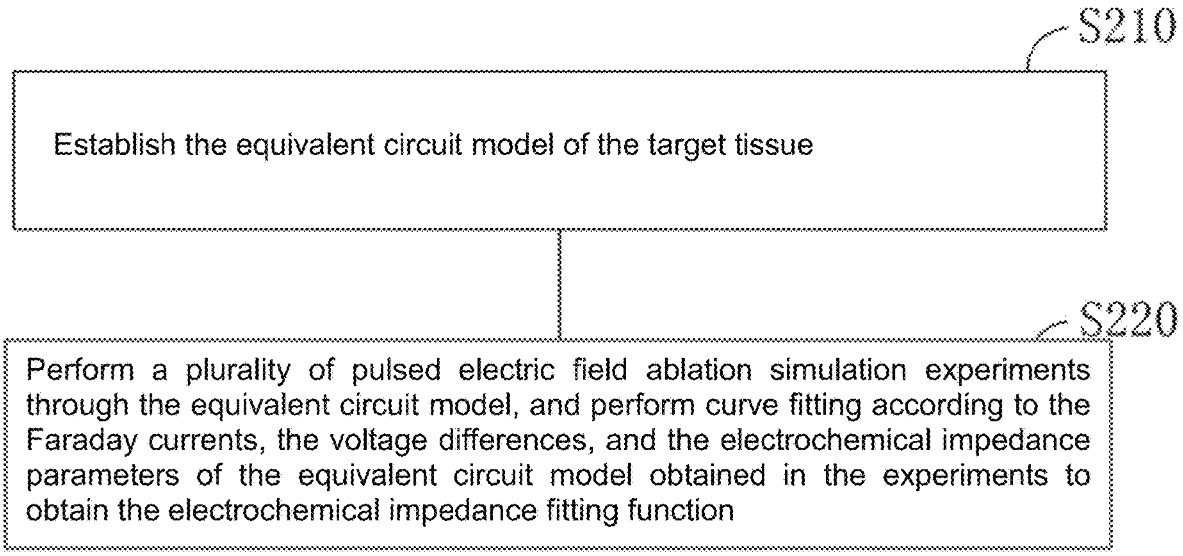
FIG. 15 is a detailed flowchart of acquiring an electrochemical impedance fitting function according to the second embodiment of the present application.

In this embodiment, as shown in FIG. 15, before the step S300, the method further includes the following steps S210 to S220.

In S210, the equivalent circuit model of the target tissue 800 is established.

In S220, a plurality of pulsed electric field ablation simulation experiments are performed through the equivalent circuit model, and curve fitting is performed according to the Faraday currents IF, the voltage differences, and the electrochemical impedance parameters of the equivalent circuit model obtained in the experiments to obtain the electrochemical impedance fitting function.

The steps S210 to S220 are used for acquiring the electrochemical impedance fitting function based on the equivalent circuit model of the target tissue 800. By establishing the equivalent circuit model, parameters in the equivalent circuit model can be accurately adjusted to obtain more sets of different data, thereby improving the accuracy of the electrochemical impedance fitting function.

Figure 16:
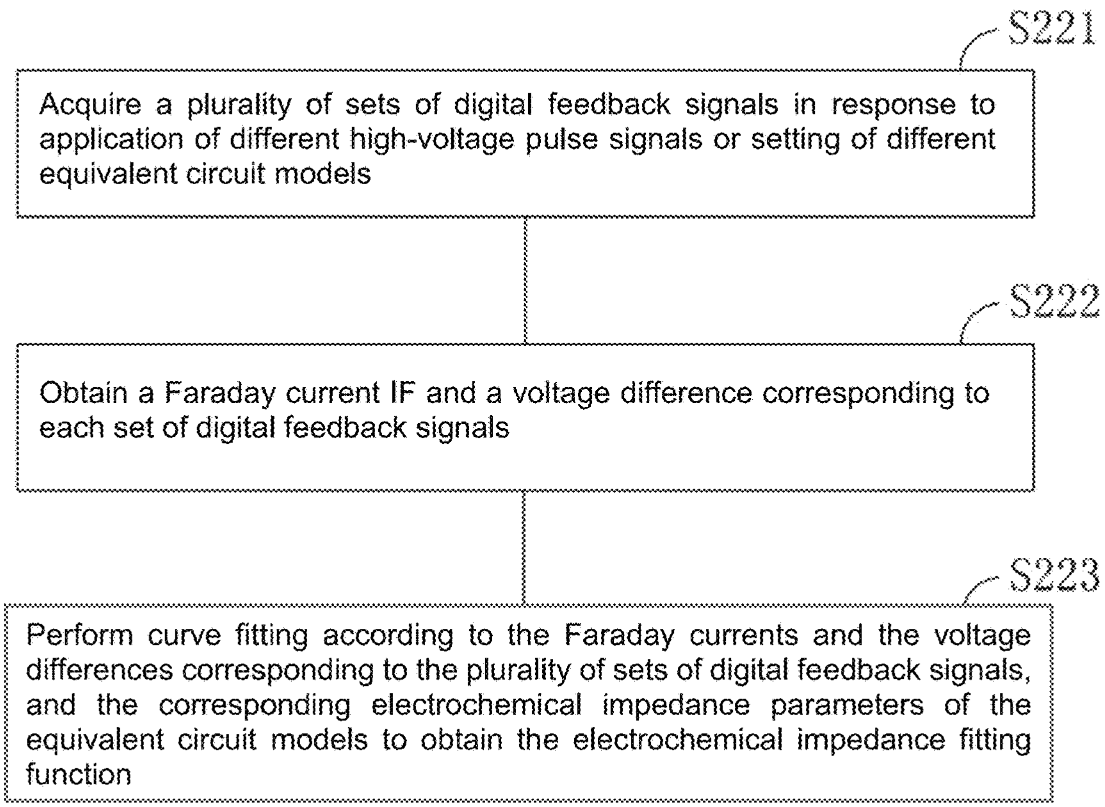
FIG. 16 is a detailed flowchart of step S220 in FIG. 15.

In this embodiment, as shown in FIG. 16, the step S220 further includes the following steps S221 to S223.

In S221, a plurality of sets of digital feedback signals in response to application of different high-voltage pulse signals or setting of different equivalent circuit models are acquired.

In S222, a Faraday current IF and a voltage difference corresponding to each set of digital feedback signals are obtained.

In S223, curve fitting is performed according to the Faraday currents IF and the voltage differences corresponding to the plurality of sets of digital feedback signals, and the corresponding electrochemical impedance parameters of the equivalent circuit models to obtain the electrochemical impedance fitting function.

Particularly, in the step S223, a method used for curve fitting includes first setting a target multivariate function, and optimizing the target multivariate function by using a search algorithm or an iterative algorithm to obtain the electrochemical impedance fitting function. Available iterative algorithms include Newton's method, Levenberg-Marquardt method, variable metric method, etc. In addition, because the electrochemical impedance model of the target tissue 800 is a complex model, the real part and the imaginary part of each impedance need to be fitted at the same time, making it more complex for the iterative algorithm to solve a nonlinear equation. In this embodiment, the target multivariate function is iterated using a multi-dimensional downhill simplex method (Nelder-Mead Method) to obtain an electrochemical impedance fitting function.

Figure 17:
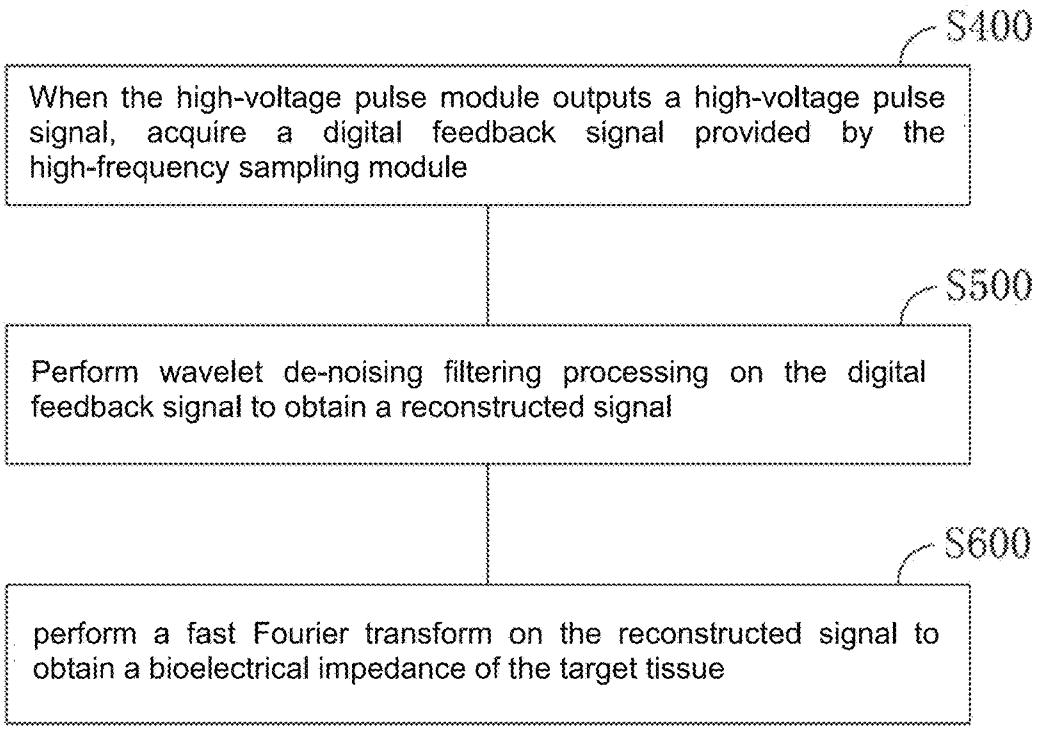
FIG. 17 is a flowchart of a biological impedance measurement method according to a third embodiment of the present application.

FIG. 17 is a flowchart of a biological impedance measurement method according to a third embodiment of the present application. For ease of description, only the part related to this embodiment is shown. A detail description is given below.

In this embodiment, the biological impedance measurement method may be applied to the tissue ablation apparatus according to any one of the foregoing embodiments, and the obtained biological impedance may be used for determining the status of bubble generation.

As shown in FIG. 17, the biological impedance measurement method includes the following steps S400 to S600.

In S400, when the high-voltage pulse module 100 outputs a high-voltage pulse signal, a digital feedback signal provided by the high-frequency sampling module 500 is acquired. The digital feedback signal includes a digital voltage signal and a digital current signal. The digital voltage signal corresponds to a voltage value between the positive output end V1 and the negative output end V2 (i.e., between two ends of the target tissue 800). The digital current signal corresponds to a value of a current flowing through the positive output end V1 or the negative output end V2 (i.e., flowing through the target tissue 800).

In S500, wavelet de-noising filtering processing is performed on the digital feedback signal to obtain a reconstructed signal. The reconstructed signal includes a reconstructed voltage signal corresponding to the digital voltage signal and a reconstructed current signal corresponding to the digital current signal.

In S600, a fast Fourier transform is performed on the reconstructed signal to obtain a bioelectrical impedance of the target tissue 800.

By the biological impedance measurement method, the impact of excessively high voltage of the high-voltage pulse signal can be avoided, and a real-time bioelectrical impedance Z(ω) can be obtained.

Particularly, the fast Fourier transform is expressed as the following formula:

$$Z(\omega) = \frac{F\{u(t)\}}{F\{i(t)\}},$$

where F{u(t)} represents the reconstructed voltage signal, and F{i(t)} represents the reconstructed current signal.

In this embodiment, the high-voltage pulse module 100, the differential sampling module 200, the voltage processing module 300, the Faraday current detection module 400, and the high-frequency sampling module 500 may be configured to implement the step S400, and the main control module 600 may be configured to implement the steps S500 and S600

Figure 18:
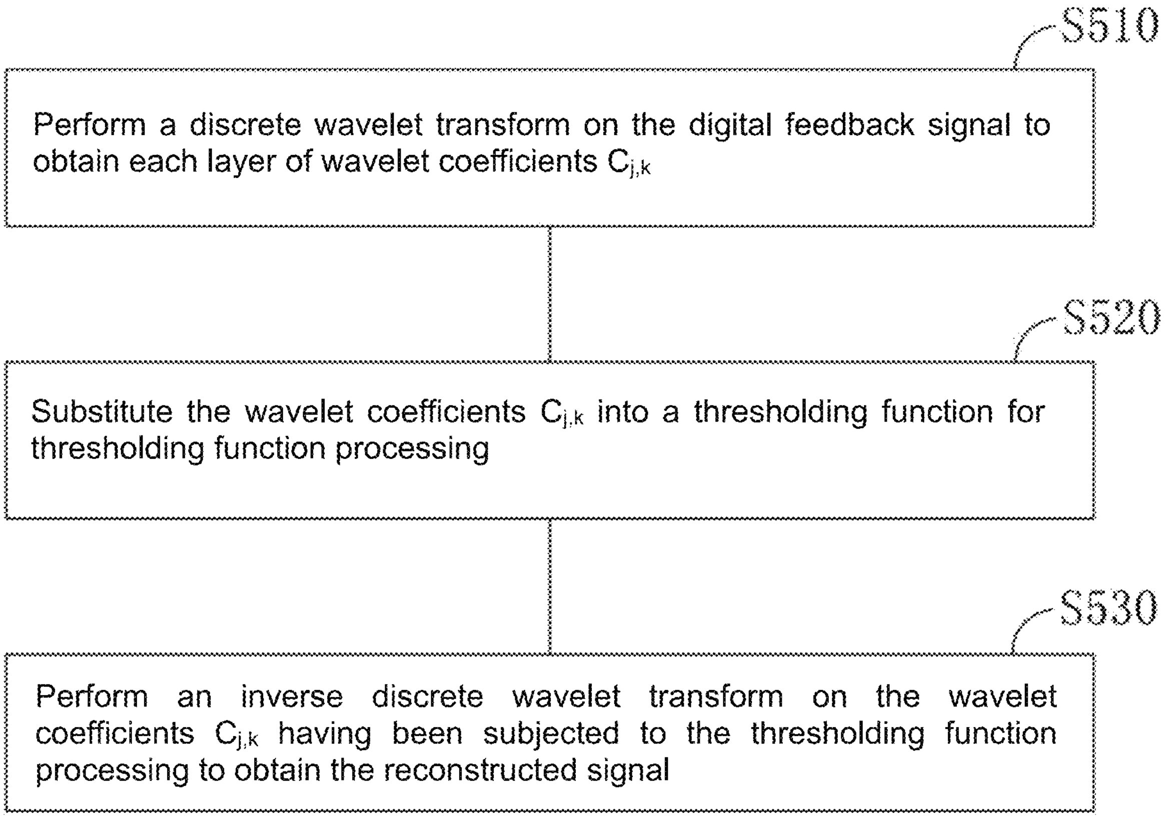
FIG. 18 is a detailed flowchart of step S500 in FIG. 17.

As shown in FIG. 18, the step S500 includes the following steps S510 to S530.

In S510, a discrete wavelet transform is performed on the digital feedback signal to obtain each layer of wavelet coefficients $C_{j,k}$. k represents a wavelet coefficient order of a $j^{th}$ layer of wavelet space. j=1, 2, . . . , J. J is a natural number, and may be set according to the actual situation.

In S520, the wavelet coefficients $C_{j,k}$ are substituted into a thresholding function for thresholding function processing.

In S530, an inverse discrete wavelet transform is performed on the wavelet coefficients $C_{j,k}$ having been subjected to the thresholding function processing to obtain the reconstructed signal.

Particularly, in the step S520, a global threshold λ or a scale-dependent threshold $\lambda_j$ need to be calculated first. j is a natural number, and may be set according to the actual situation. A formula for calculating the global threshold λ is: $\lambda=\sqrt{2\ln(n)}$, where n represents a global signal length. A formula for calculating the scale-dependent threshold $\lambda_j$ is: $\lambda_j=\sigma_j\sqrt{2\ln(n_j)}$, where $n_j$ represents a signal length of each layer of wavelet coefficients, and the coefficient $\sigma_j$ may be determined empirically or may be determined by the following formula: $\sigma_j$=MAD($|C_{j,k}|$, $0\leq k\leq 2^{j-1}-1$)/q, where MAD( ) represents finding the median of values in parentheses, MAD($|C_{j,k}|$, $0\leq k\leq 2^{j-1}-1$) is a median in a wavelet coefficient sequence, and the coefficient q may be empirically selected from a range of 0.4 to 1. Further, the value of q may range from 0.6 to 0.8. The global threshold λ is used in this embodiment. Whether to use the global threshold λ or the scale-dependent threshold $\lambda_j$ may be determined according to requirements in practice.

Figure 19:
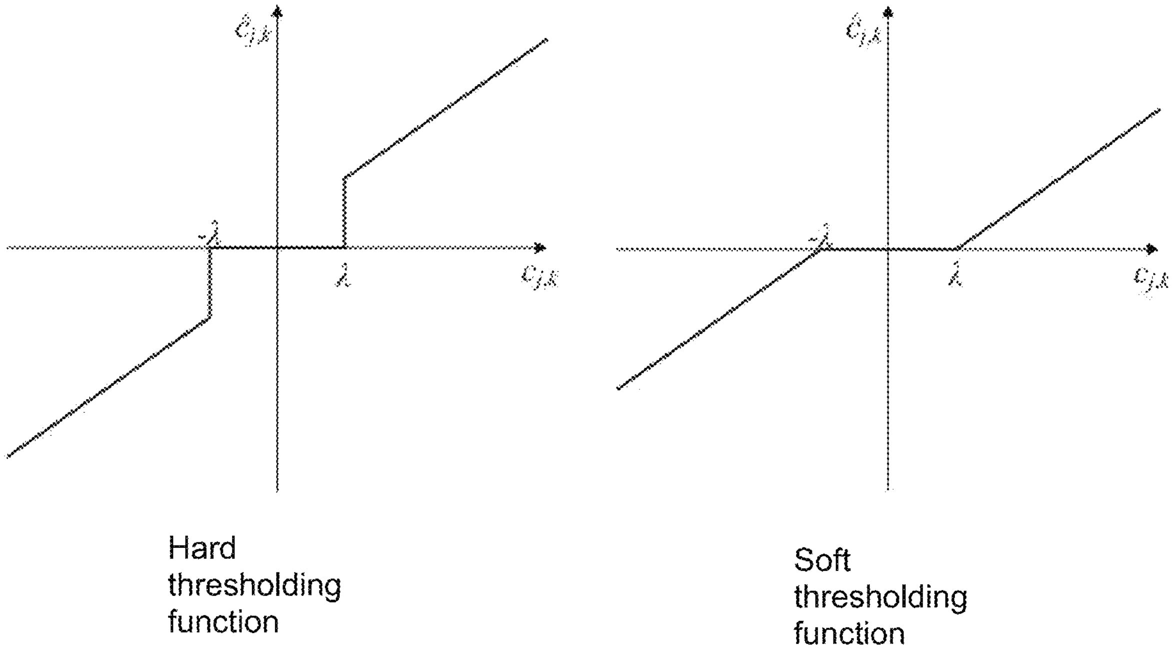
FIG. 19 is a schematic view of a hard thresholding function and a soft thresholding function.

In the step S520, the thresholding function includes a hard thresholding function and a soft thresholding function. FIG. 19 is a schematic view of the hard thresholding function and the soft thresholding function. The hard thresholding function only retains the wavelet coefficients having an absolute value greater than the global threshold λ, the retained wavelet coefficients are the same as original coefficients, and the wavelet coefficients having an absolute value less than or equal to the global threshold λ are set to zero. The hard thresholding function is expressed as the following formula:

$$\eta_h(c_{j,k}, \lambda) = \begin{cases} c_{j,k}, & |c_{j,k}| \geq \lambda \\ 0, & |c_{j,k}| < \lambda \end{cases}$$

The soft thresholding function also sets the wavelet coefficients having an absolute value less than or equal to the global threshold λ to zero, but uses λ to shrink the wavelet coefficients λ having an absolute value greater than the global threshold λ. The soft thresholding function is expressed as the following formula:

$$\eta_s(c_{j,k}, \lambda) = \begin{cases} c_{j,k} - \lambda, & c_{j,k} \geq \lambda \\ 0, & c_{j,k} < \lambda \\ c_{j,k} + \lambda, & c_{j,k} \leq -\lambda \end{cases}$$

When the hard thresholding function is used in step the S520, the thresholding function is discontinuous at the global threshold λ, which leads to a large variance, resulting in that the reconstructed signal has additional oscillations, and is not as smooth as the original signal. After the step S530 is performed, a reconstructed signal having a waveform closer to the waveform of the digital feedback signal can be obtained. When the soft thresholding function is used in the step S520, the soft thresholding function usually makes the denoised signal smoother, but causes the loss of some features of the signal, affects the degree by which the reconstructed signal approximates the original signal. After the step S530 is performed, a reconstructed signal having a waveform smoother than the waveform of the digital feedback signal can be obtained. The inverse discrete wavelet transform is expressed as the following formula: $f(t)=\Sigma_{j,k}c_{j,k}\psi_{j,k}(t)$, where $\psi_{j,k}(t)$ represents a scaling function corresponding to each wavelet coefficient $C_{j,k}$.

It should be understood that the sequence numbers of the steps in the foregoing embodiments do not imply an execution order, and the execution order of the processes should be determined by the functions and internal logic of the processes, and should not constitute any limitation on the implementation processes of the embodiments of the present application.

Figure 20:
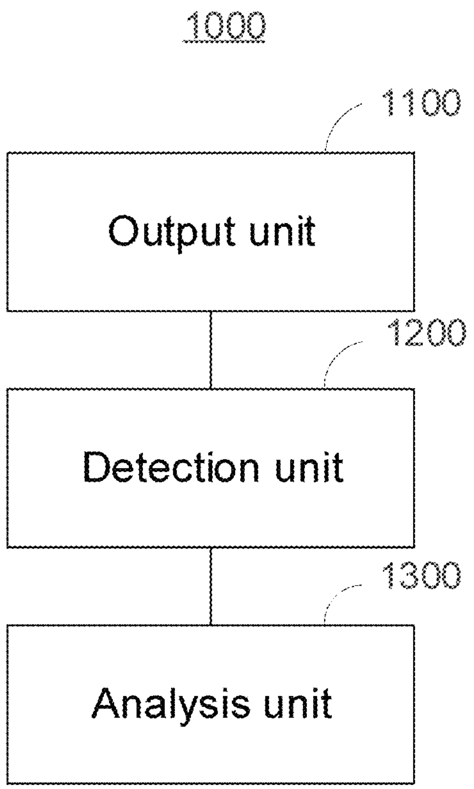
FIG. 20 is a schematic view illustrating the principle of an electrochemical impedance measurement apparatus according to a fourth embodiment of the present application.

FIG. 20 is a schematic view illustrating the principle of an electrochemical impedance measurement apparatus according to a fourth embodiment of the present application. For ease of description, only the part related to this embodiment is shown. A detail description is given below.

As shown in FIG. 20, the electrochemical impedance measurement apparatus 1000 may be applied to the tissue ablation apparatus according to any one of the foregoing embodiments, and execute the biological impedance measurement method according to any one of the foregoing embodiments, to acquire an electrochemical impedance parameter of a target tissue 800. The electrochemical impedance measurement apparatus 1000 includes an output unit 1100, a detection unit 1200, and an analysis unit 1300.

The output unit 1100 is configured to apply a high-voltage pulse signal to the target tissue 800 through an electrode pair. The detection unit 1200 is configured to acquire a Faraday current and a voltage difference between the electrode pair from the side of the electrode pair. The analysis unit 1300 is configured to obtain the electrochemical impedance parameter corresponding to the target tissue 800 by the Faraday current, the voltage difference and an electrochemical impedance fitting function.

The electrochemical impedance fitting function is obtained by fitting electrical parameters obtained in a pulsed electric field ablation simulation experiment performed based on an equivalent circuit model of the target tissue 800. The equivalent circuit model is as shown in FIG. 14. In this embodiment, electrochemical impedance parameters in the equivalent circuit model include a tissue and solution resistance RΩ, a Faraday impedance Zf, an electric double layer capacitance Cd, a parasitic capacitance Cp, and a parasitic inductance Ls. The Faraday impedance Zf represents a nonlinear impedance in the electrochemical reaction system, and is related to the frequency of the high-voltage pulse signal. The electric double layer capacitance Cd represents an equivalent capacitance of ablation electrodes in the blood. The parasitic capacitance Cp and the parasitic inductance Ls respectively represent a parasitic capacitance and a parasitic inductance of the entire circuit.

It should be noted that, the electrochemical impedance model of the target tissue 800 is complex, includes a large number of parameters that cannot be directly detected. Therefore, to acquire the electrochemical impedance parameter of the target tissue 800 in real time, the method of acquiring the electrochemical impedance fitting function through curve fitting in this embodiment only requires the collection of the Faraday current IF and the voltage difference between the electrode pair that can be easily detected. The voltage difference between the electrode pair may be replaced with the voltage difference between the first output end V1 and the second output end V2. In this way, a real-time electrochemical impedance parameter can be obtained, and the status of bubble generation can be determined according to the real-time electrochemical impedance parameter.

Figure 21:
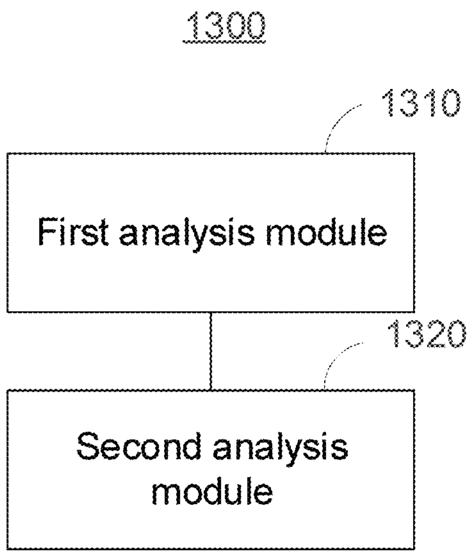
FIG. 21 is a principle schematic view of an analysis unit according to the fourth embodiment of the present application.

As shown in FIG. 21, in an embodiment, the analysis unit 1300 includes a first analysis module 1310 and a second analysis module 1320.

The first analysis module 1310 is configured to establish the equivalent circuit model of the target tissue 800. The second analysis module 1320 is configured to perform a plurality of pulsed electric field ablation simulation experiments through the equivalent circuit model, and perform curve fitting according to the Faraday currents, the voltage differences, and the electrochemical impedance parameters of the equivalent circuit model obtained in the experiments to obtain the electrochemical impedance fitting function.

The first analysis module 1310 and the second analysis module 1320 are configured to acquire the electrochemical impedance fitting function based on the equivalent circuit model of the target tissue 800. By establishing the equivalent circuit model, parameters in the equivalent circuit model can be accurately adjusted to obtain more sets of different data, thereby improving the accuracy of the electrochemical impedance fitting function.

Figure 22:
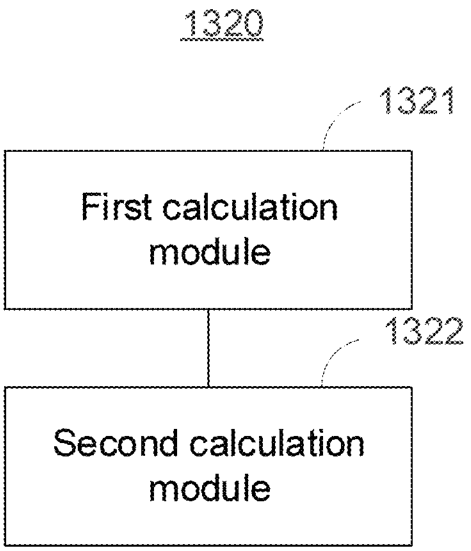
FIG. 22 is a principle schematic view of a second analysis module according to the fourth embodiment of the present application.

As shown in FIG. 22, in an embodiment, the second analysis module 1320 includes a first calculation module 1321 and a second calculation module 1322.

The first calculation module 1321 is configured to acquire a plurality of sets of digital feedback signals in response to application of different high-voltage pulse signals or setting of different equivalent circuit models. The second calculation module 1322 is configured to obtain a Faraday current and a voltage difference corresponding to each set of digital feedback signals. The second calculation module 1322 is further configured to perform curve fitting according to the Faraday currents and the voltage differences corresponding to the plurality of sets of digital feedback signals, and the corresponding electrochemical impedance parameters of the equivalent circuit models to obtain the electrochemical impedance fitting function.

Particularly, a method used by the second calculation module 1322 for curve fitting includes first setting a target multivariate function, and optimizing the target multivariate function by using a search algorithm or an iterative algorithm to obtain the electrochemical impedance fitting function. Available iterative algorithms include Newton's method, Levenberg-Marquardt method, variable metric method, etc. In addition, because the electrochemical impedance model of the target tissue 800 is a complex model, the real part and the imaginary part of each impedance need to be fitted at the same time, making it more complex for the iterative algorithm to solve a nonlinear equation. In this embodiment, the target multivariate function is iterated using a multi-dimensional downhill simplex method (Nelder-Mead Method) to obtain an electrochemical impedance fitting function.

A person skilled in the art can clearly understand that for convenience and brevity of description, the description is given by using the above division of functional units or modules as an example. In practical applications, the above functions may be assigned to be implemented by different functional units or modules according to needs, i.e., the internal structure of the apparatus may be divided into different functional units or modules to implement all or part of the functions described above. Functional units or modules in the embodiments may be integrated into one processing unit, or each of the units may exist alone physically, or two or more units may be integrated into one unit. The integrated unit may be implemented in the form of hardware, or may be implemented in the form of a software functional unit. In addition, the specific names of the functional units or modules are merely for the convenience of distinguishing from each other, and are not intended to limit the protection scope of the present application. For detailed working processes of the units and modules in the system, reference may be made to the corresponding processes in the foregoing method embodiments, and the details will not be described herein again.

In the above embodiments, the description in each embodiment has its own focus. For parts that are not detailed or set forth in one embodiment, reference can be made to the relevant descriptions in other embodiments.

The foregoing embodiments are merely intended for describing the technical solutions of the present application, but not for limiting the present application. It should be understood by a person of ordinary skill in the art that although the present application has been described in detail with reference to the foregoing embodiments, modifications can be made to the technical solutions described in the foregoing embodiments, or equivalent replacements can be made to some technical features in the technical solutions, as long as such modifications or replacements do not cause the essence of corresponding technical solutions to depart from the spirit and scope of the technical solutions of the embodiments of the present application. All such modifications or replacements shall fall within the scope of the present application.

The invention claimed is:

1. A tissue ablation apparatus, comprising:

a high-voltage pulse module configured to generate a high-voltage pulse signal according to a pulse control signal, and apply the high-voltage pulse signal to a target tissue through a first output end and a second output end of the high-voltage pulse module wherein the first output end is configured to connect to a first electrode and the second output end is configured to connect to a second electrode;

a Faraday current detection module arranged between the high-voltage pulse module and the first electrode and the second electrode and configured to generate a sampling signal based on a current flowing through the first electrode and a current flowing through the second electrode;

a differential sampling module connected to the first output end and the second output end of the high-voltage pulse module and configured to generate and output a first feedback voltage and a second feedback voltage according to a voltage change of the first output end and a voltage change of the second output end respectively;

a voltage processing module connected to the differential sampling module and configured to generate and output a voltage feedback signal according to the first feedback voltage and the second feedback voltage, wherein the voltage feedback signal corresponds to a voltage difference between the first output end and the second output end;

a high-frequency sampling module, connected to the voltage processing module and the Faraday current detection module, and configured to generate and output a digital feedback signal according to the voltage feedback signal and the sampling signal; and a main control module connected to the high-voltage pulse module and the high-frequency sampling module and configured to obtain a Faraday current and the voltage difference between the first output end and the second output end according to the received digital feedback signal, obtain an electrochemical impedance parameter of the target tissue by the Faraday current, the voltage difference between the first output end and the second output end and an electrochemical impedance fitting function, and generate the pulse control signal according to the electrochemical impedance parameter, wherein the electrochemical impedance fitting function is obtained by fitting electrical parameters obtained in a pulsed electric field ablation simulation experiment performed based on an equivalent circuit model of the target tissue.

2. The tissue ablation apparatus according to claim 1, wherein the Faraday current detection module comprises a first sampling resistor, a second sampling resistor, a first differential voltage sampling unit, and a second differential voltage sampling unit;

the first sampling resistor is connected in series between the first output end and the first electrode, the second sampling resistor is connected in series between the second output end and the second electrode, the first differential voltage sampling unit is connected to the high-frequency sampling module and two ends of the first sampling resistor, the second differential voltage sampling unit is connected to the high-frequency sampling module and two ends of the second sampling resistor, the first differential voltage sampling unit is configured to collect a first voltage difference between the two ends of the first sampling resistor, the second differential voltage sampling unit is configured to collect a second voltage difference between the two ends of the second sampling resistor, and the sampling signal comprises the first voltage difference and the second voltage difference; and the high-frequency sampling module is configured to generate and output the digital feedback signal based on the first voltage difference and the second voltage difference, and the main control module is configured to obtain the Faraday current participating in an electrochemical reaction of the target tissue based on the digital feedback signal, a resistance value of the first sampling resistor, and a resistance value of the second sampling resistor.

3. The tissue ablation apparatus according to claim 2, wherein the high-frequency sampling module comprises a filtering and shaping unit, a measuring range selection unit, an analog-to-digital conversion unit, and a sampling processing unit connected in sequence, the filtering and shaping unit is connected to the voltage processing module and the Faraday current detection module, the sampling processing unit is connected to the main control module and the measuring range selection unit, the filtering and shaping unit is configured to convert the received voltage feedback signal and the received sampling signal according to a set measuring range to obtain a corresponding analog signal, the AD conversion unit is configured to sample the analog signal according to a preset frequency to obtain a digital signal, and the sampling processing unit is configured to generate a digital feedback signal according to the digital signal outputted by the AD conversion unit, and configure a measuring range of the measuring range selection unit according to the digital feedback signal.

4. The tissue ablation apparatus according to claim 1, wherein the Faraday current detection module comprises a first current sampling probe and a second current sampling probe, the first current sampling probe is arranged on a wire between the first output end and the first electrode and is electrically connected to the high-frequency sampling module, and the second current sampling probe is arranged on a wire between the second output end and the second electrode and is electrically connected to the high-frequency sampling module;

the first current sampling probe is configured to generate a first current feedback signal based on a current flowing through the wire between the first output end and the first electrode and output the first current feedback signal to the high-frequency sampling module, the second current sampling probe is configured to generate a second current feedback signal based on a current flowing through the wire between the second output end and the second electrode and output the second current feedback signal to the high-frequency sampling module, and the sampling signal comprises the first current feedback signal and the second current feedback signal; and the high-frequency sampling module is configured to generate and output the digital feedback signal based on the first current feedback signal and the second current feedback signal, and the main control module is configured to obtain the Faraday current participating in the electrochemical reaction of the target tissue based on the digital feedback signal.

5. The tissue ablation apparatus according to claim 4, wherein the high-frequency sampling module comprises a filtering and shaping unit, a measuring range selection unit, an analog-to-digital conversion unit, and a sampling processing unit connected in sequence, the filtering and shaping unit is connected to the voltage processing module and the Faraday current detection module, the sampling processing unit is connected to the main control module and the measuring range selection unit, the filtering and shaping unit is configured to convert the received voltage feedback signal and the received sampling signal according to a set measuring range to obtain a corresponding analog signal, the AD conversion unit is configured to sample the analog signal according to a preset frequency to obtain a digital signal, and the sampling processing unit is configured to generate a digital feedback signal according to the digital signal outputted by the AD conversion unit, and configure a measuring range of the measuring range selection unit according to the digital feedback signal.

6. The tissue ablation apparatus according to claim 1, wherein the differential sampling module comprises a first sampling branch and a second sampling branch, the first sampling branch is connected between the first output end and the voltage processing module, the second sampling branch is connected between the second output end and the voltage processing module, the first sampling branch is configured to generate the first feedback voltage, and the second sampling branch is configured to generate the second feedback voltage.

7. The tissue ablation apparatus according to claim 6, wherein the first sampling branch comprises a first broadband voltage divider unit and a first single-ended amplification unit, the first broadband voltage divider unit is connected to the first output end and the first single-ended amplification unit, the first single-ended amplification unit is further connected to the voltage processing module, and the first single-ended amplification unit is configured to generate the first feedback voltage according to a voltage obtained through voltage division by the first broadband voltage divider unit.

8. The tissue ablation apparatus according to claim 7, wherein the second sampling branch comprises a second broadband voltage divider unit and a second single-ended amplification unit, the second broadband voltage divider unit is connected to the first output end and the second single-ended amplification unit, the second single-ended amplification unit is further connected to the voltage processing module, and the second single-ended amplification unit is configured to generate the second feedback voltage according to a voltage obtained through voltage division by the second broadband voltage divider unit.

9. The tissue ablation apparatus according to claim 8, wherein the first sampling branch further comprises a first protection unit, the second sampling branch further comprises a second protection unit, the first protection unit is connected between the first broadband voltage divider unit and the first single-ended amplification unit, and the second protection unit is connected between the second broadband voltage divider unit and the second single-ended amplification unit; and the first protection unit is configured to limit an amplitude of a voltage to be transmitted to the first single-ended amplification unit, and the second protection unit is configured to limit an amplitude of a voltage to be transmitted to the second single-ended amplification unit.

10. The tissue ablation apparatus according to claim 7, wherein the high-frequency sampling module comprises a filtering and shaping unit, a measuring range selection unit, an analog-to-digital conversion unit, and a sampling processing unit connected in sequence, the filtering and shaping unit is connected to the voltage processing module and the Faraday current detection module, the sampling processing unit is connected to the main control module and the measuring range selection unit, the filtering and shaping unit is configured to convert the received voltage feedback signal and the received sampling signal according to a set measuring range to obtain a corresponding analog signal, the AD conversion unit is configured to sample the analog signal according to a preset frequency to obtain a digital signal, and the sampling processing unit is configured to generate a digital feedback signal according to the digital signal outputted by the AD conversion unit, and configure a measuring range of the measuring range selection unit according to the digital feedback signal.

11. The electrochemical impedance measurement method according to claim 10, wherein obtaining of the electrochemical impedance fitting function by fitting electrical parameters obtained in the pulsed electric field ablation simulation experiment performed based on the equivalent circuit model of the target tissue comprises:

establishing the equivalent circuit model of the target tissue; and performing a plurality of pulsed electric field ablation simulation experiments through the equivalent circuit model, and performing curve fitting according to the Faraday currents, the voltage differences, and the electrochemical impedance parameters of the equivalent circuit model obtained in the experiments to obtain the electrochemical impedance fitting function.

12. The electrochemical impedance measurement method according to claim 11, wherein the step of performing the plurality of pulsed electric field ablation simulation experiments through the equivalent circuit model, and performing curve fitting according to the Faraday currents, the voltage differences, and the electrochemical impedance parameters of the equivalent circuit model obtained in the experiments to obtain the electrochemical impedance fitting function comprises:

acquiring a plurality of sets of digital feedback signals in response to application of different high-voltage pulse signals or setting of different equivalent circuit models;

obtaining a Faraday current and a voltage difference corresponding to each set of digital feedback signals, and performing curve fitting according to the Faraday currents and the voltage differences corresponding to the plurality of sets of digital feedback signals, and corresponding electrochemical impedance parameters of the equivalent circuit models to obtain the electrochemical impedance fitting function.

13. The tissue ablation apparatus according to claim 6, wherein the high-frequency sampling module comprises a filtering and shaping unit, a measuring range selection unit, an analog-to-digital conversion unit, and a sampling processing unit connected in sequence, the filtering and shaping unit is connected to the voltage processing module and the Faraday current detection module, the sampling processing unit is connected to the main control module and the measuring range selection unit, the filtering and shaping unit is configured to convert the received voltage feedback signal and the received sampling signal according to a set measuring range to obtain a corresponding analog signal, the AD conversion unit is configured to sample the analog signal according to a preset frequency to obtain a digital signal, and the sampling processing unit is configured to generate a digital feedback signal according to the digital signal outputted by the AD conversion unit, and configure a measuring range of the measuring range selection unit according to the digital feedback signal.

14. The tissue ablation apparatus according to claim 1, wherein the voltage processing module comprises a differential amplification unit and a third protection unit connected to the differential amplification unit, the differential amplification unit is further connected to the differential sampling module, the differential amplification unit is configured to generate the voltage feedback signal according to the first feedback voltage and the second feedback voltage, the third protection unit is further connected to the high-frequency sampling module, and the third protection unit is configured to limit an amplitude of a voltage to be transmitted to the high-frequency sampling module.

15. The tissue ablation apparatus according to claim 14, wherein the high-frequency sampling module comprises a filtering and shaping unit, a measuring range selection unit, an analog-to-digital conversion unit, and a sampling processing unit connected in sequence, the filtering and shaping unit is connected to the voltage processing module and the Faraday current detection module, the sampling processing unit is connected to the main control module and the measuring range selection unit, the filtering and shaping unit is configured to convert the received voltage feedback signal and the received sampling signal according to a set measuring range to obtain a corresponding analog signal, the AD conversion unit is configured to sample the analog signal according to a preset frequency to obtain a digital signal, and the sampling processing unit is configured to generate a digital feedback signal according to the digital signal outputted by the AD conversion unit, and configure a measuring range of the measuring range selection unit according to the digital feedback signal.

16. The tissue ablation apparatus according to claim 1, wherein the high-frequency sampling module comprises a filtering and shaping unit, a measuring range selection unit, an analog-to-digital conversion unit, and a sampling processing unit connected in sequence, the filtering and shaping unit is connected to the voltage processing module and the Faraday current detection module, the sampling processing unit is connected to the main control module and the measuring range selection unit, the filtering and shaping unit is configured to convert the received voltage feedback signal and the received sampling signal according to a set measuring range to obtain a corresponding analog signal, the AD conversion unit is configured to sample the analog signal according to a preset frequency to obtain a digital signal, and the sampling processing unit is configured to generate a digital feedback signal according to the digital signal outputted by the AD conversion unit, and configure a measuring range of the measuring range selection unit according to the digital feedback signal.

17. An electrochemical impedance measurement apparatus, applied to a tissue ablation apparatus to acquire an electrochemical impedance parameter of a target tissue, the electrochemical impedance measurement apparatus comprising:

an output unit, configured to apply a high-voltage pulse signal to the target tissue through an electrode pair;

a detection unit, configured to acquire a Faraday current and a voltage difference between the electrode pair from the side of the electrode pair; and an analysis unit, configured to obtain the electrochemical impedance parameter corresponding to the target tissue by the Faraday current, the voltage difference and an electrochemical impedance fitting function, wherein the electrochemical impedance fitting function is obtained by fitting electrical parameters obtained in a pulsed electric field ablation simulation experiment performed based on an equivalent circuit model of the target tissue.

18. The electrochemical impedance measurement apparatus according to claim 17, wherein the analysis unit comprises:

a first analysis module, configured to establish the equivalent circuit model of the target tissue; and a second analysis module, configured to perform a plurality of pulsed electric field ablation simulation experiments through the equivalent circuit model, and perform curve fitting according to the Faraday currents, the voltage differences, and the electrochemical impedance parameters of the equivalent circuit model obtained in the experiments to obtain the electrochemical impedance fitting function.

19. The electrochemical impedance measurement apparatus according to claim 18, wherein the second analysis module comprises:

a first calculation module, configured to acquire a plurality of sets of digital feedback signals in response to application of different high-voltage pulse signals or setting of different equivalent circuit models; and a second calculation module, configured to obtain a Faraday current and a voltage difference corresponding to each set of digital feedback signals, and perform curve fitting according to the Faraday currents, the voltage differences, and corresponding electrochemical impedance parameters of the equivalent circuit models to obtain the electrochemical impedance fitting function.

20. A electrochemical impedance measurement method, applied to a tissue ablation apparatus to acquire an electrochemical impedance parameter of a target tissue, the electrochemical impedance measurement method comprising:

applying a high-voltage pulse signal to the target tissue through an electrode pair;

acquiring a Faraday current and a voltage difference between the electrode pair from the side of the electrode pair; and obtaining the electrochemical impedance parameter corresponding to the target tissue by the Faraday current, the voltage difference and an electrochemical impedance fitting function, wherein the electrochemical impedance fitting function is obtained by fitting electrical parameters obtained in a pulsed electric field ablation simulation experiment performed based on an equivalent circuit model of the target tissue.

* * * * *